United States Patent
Hansen

(10) Patent No.: US 8,337,842 B2
(45) Date of Patent: Dec. 25, 2012

(54) MONOCLONAL ANTIBODIES

(75) Inventor: Geneviève Hansen, Del Mar, CA (US)

(73) Assignee: Vet Therapeutics, Inc., Del Mar, CA (US)

( * ) Notice: Subject to any disclaimer, the term of this patent is extended or adjusted under 35 U.S.C. 154(b) by 79 days.

(21) Appl. No.: 12/584,390

(22) Filed: Sep. 4, 2009

(65) Prior Publication Data

US 2010/0061988 A1    Mar. 11, 2010

Related U.S. Application Data

(60) Provisional application No. 61/094,333, filed on Sep. 4, 2008, provisional application No. 61/163,188, filed on Mar. 25, 2009.

(51) Int. Cl.
*A61K 39/395*    (2006.01)
*C07K 16/00*    (2006.01)

(52) U.S. Cl. .................................. 424/133.1; 530/387.3

(58) Field of Classification Search ................ 424/133.1; 530/387.3
See application file for complete search history.

(56) References Cited

U.S. PATENT DOCUMENTS

| | | | |
|---|---|---|---|
| 2002/0041847 A1 | 4/2002 | Goldenberg |
| 2005/0271662 A1 | 12/2005 | Beall |
| 2007/0004909 A1 | 1/2007 | Johnson |
| 2008/0188401 A1 | 8/2008 | Cruwys |

FOREIGN PATENT DOCUMENTS

WO   WO 2004/003019   *   6/2003

OTHER PUBLICATIONS

Rudikoff et al (Proc Natl Acad Sci USA 1982 vol. 79 p. 1979).*
MacCallum et al. (J. Mol. Biol. (1996) 262:732-745).*
De Pascalis et al. The Journal of Immunology (2002) 169, 3076-3084.*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. J. Mol. Bio. (1999) 293, 865-881.*
Wu et al. (J. Mol. Biol. (1999) 294, 151-162).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Das et al., "Evolutionary dynamics of the immunoglobulin heavy chain variable region genes in vertebrates", Immunogenetics, 60: 47-55 (2008).
Das et al., "Evolutionary redefinition of immunoglobulin light chain isotypes in tetrapods using molecular markers" Proc. Nat'l. Acad. Sci. 105 (43): 16647-16652 (2008).
Day, M.J et al. "Tissue Immunglobulin G subclasses observed in immune-mediated dermatopathy, deep pyoderma and hypersensitivity dermatitis in dogs", Vet. Sci. 58: 82-89 (1995).
Fayngerts, Alexander, Najakshin, and Taranin, "Species-specific evolution of the FcR family in endothermic vertebrates." Immunogenetics 59: 493-506 (2007).
Jubala et al. "CD20 Expression in Normal Canine B Cells and in Canine non-Hodgkin Lymphoma." Vet Pathol 42: 468-476 (2005).
Mazza, et al. "The Separation and Identification by Monoclonal Antibodies of Dog IgG Fractions", J. Imm. Meth. 161: 193-203 (1993).
Tang et al., "Cloning and characterization of cDNAs encoding four different canine immunoglobulin gamma chains" Vet. Imm. Immunopath. 80: 259-270 (2001).
Written Opinion (PCT/US2009/004997), Vet Therapeutics, Inc.

* cited by examiner

*Primary Examiner* — Lynn Bristol
(74) *Attorney, Agent, or Firm* — Hoxie & Associates, LLC

(57) ABSTRACT

The invention provides heterochimeric antibodies and/or fragments thereof comprising (i) hypervariable region sequences wholly or substantially corresponding to sequences found in antibodies from a donor species; (ii) constant region sequences wholly or substantially corresponding to sequences found in antibodies from a target species which is different from the donor species; and (iii) heavy and/or light chain variable framework sequences which contain at least three non-CDR residues corresponding to sequences found in antibodies from a target species and at least three contiguous non-CDR residues corresponding to sequences found in antibodies from a donor species. The invention further provides antibody to canine or feline or equine antigens, e.g., CD20 or CD52, and methods of making and using antibodies as described.

31 Claims, No Drawings

SEQUENCE LISTING

<160> NUMBER OF SEQ ID NOS: 90

<210> SEQ ID NO 1
<211> LENGTH: 10
<212> TYPE: PRT
<213> ORGANISM: Canis familiaris

<400> SEQUENCE: 1

Phe Gly Gly Gly Thr His Leu Thr Val Leu
 1               5                  10

<210> SEQ ID NO 2
<211> LENGTH: 10
<212> TYPE: PRT
<213> ORGANISM: Canis familiaris

<400> SEQUENCE: 2

Phe Gly Ser Gly Thr Pro Leu Thr Val Leu
 1               5                  10

<210> SEQ ID NO 3
<211> LENGTH: 11
<212> TYPE: PRT
<213> ORGANISM: Canis familiaris

<400> SEQUENCE: 3

Phe Gly Ala Gly Thr Lys Val Glu Leu Ile Arg
 1               5                  10

<210> SEQ ID NO 4
<211> LENGTH: 11
<212> TYPE: PRT
<213> ORGANISM: Canis familiaris

<400> SEQUENCE: 4

Phe Gly Gln Gly Thr Arg Leu Glu Val Arg Arg
 1               5                  10

<210> SEQ ID NO 5
<211> LENGTH: 10
<212> TYPE: PRT
<213> ORGANISM: Canis familiaris

<400> SEQUENCE: 5

Phe Gly Ser Gly Thr Gln Leu Thr Val Leu
 1               5                  10

<210> SEQ ID NO 6
<211> LENGTH: 10
<212> TYPE: PRT
<213> ORGANISM: Canis familiaris

<400> SEQUENCE: 6

Phe Gly Arg Gly Thr Gln Leu Thr Val Leu
 1               5                  10

<210> SEQ ID NO 7
<211> LENGTH: 10
<212> TYPE: PRT
<213> ORGANISM: Canis familiaris

<400> SEQUENCE: 7

Phe Gly Glu Gly Thr Gln Leu Thr Val Leu
1               5                   10

<210> SEQ ID NO 8
<211> LENGTH: 10
<212> TYPE: PRT
<213> ORGANISM: Canis familiaris

<400> SEQUENCE: 8

Phe Gly Gly Gly Thr Lys Leu Glu Ile Lys
1               5                   10

<210> SEQ ID NO 9
<211> LENGTH: 10
<212> TYPE: PRT
<213> ORGANISM: Canis familiaris

<400> SEQUENCE: 9

Phe Gly Lys Gly Thr His Leu Glu Ile Lys
1               5                   10

<210> SEQ ID NO 10
<211> LENGTH: 10
<212> TYPE: PRT
<213> ORGANISM: Canis familiaris

<400> SEQUENCE: 10

Phe Gly Gln Gly Thr Lys Val Glu Ile Lys
1               5                   10

<210> SEQ ID NO 11
<211> LENGTH: 10
<212> TYPE: PRT
<213> ORGANISM: Canis familiaris

<400> SEQUENCE: 11

Phe Gly Gln Gly Thr Lys Leu Glu Ile Lys
1               5                   10

<210> SEQ ID NO 12
<211> LENGTH: 10
<212> TYPE: PRT
<213> ORGANISM: Canis familiaris

<400> SEQUENCE: 12

Phe Gly Ala Gly Thr Lys Val Glu Ile Lys
1               5                   10

<210> SEQ ID NO 13
<211> LENGTH: 11
<212> TYPE: PRT
<213> ORGANISM: Canis familiaris

<400> SEQUENCE: 13

Trp Gly Gln Gly Thr Leu Val Thr Val Ser Ser
1               5                   10

<210> SEQ ID NO 14

```
<211> LENGTH: 11
<212> TYPE: PRT
<213> ORGANISM: Canis familiaris

<400> SEQUENCE: 14

Trp Gly Gln Gly Ala Leu Val Thr Val Ser Ser
1               5                   10

<210> SEQ ID NO 15
<211> LENGTH: 11
<212> TYPE: PRT
<213> ORGANISM: Canis familiaris

<400> SEQUENCE: 15

Trp Gly Pro Gly Thr Ser Leu Phe Val Ser Ser
1               5                   10

<210> SEQ ID NO 16
<211> LENGTH: 11
<212> TYPE: PRT
<213> ORGANISM: Canis familiaris

<400> SEQUENCE: 16

Trp Gly Leu Gly Thr Leu Val Thr Val Ser Ser
1               5                   10

<210> SEQ ID NO 17
<211> LENGTH: 11
<212> TYPE: PRT
<213> ORGANISM: Canis familiaris

<400> SEQUENCE: 17

Trp Gly Pro Gly Thr Ser Leu Phe Val Ser Ser
1               5                   10

<210> SEQ ID NO 18
<211> LENGTH: 11
<212> TYPE: PRT
<213> ORGANISM: Canis familiaris

<400> SEQUENCE: 18

Trp Gly Gln Gly Thr Leu Val Thr Val Ser Pro
1               5                   10

<210> SEQ ID NO 19
<211> LENGTH: 11
<212> TYPE: PRT
<213> ORGANISM: Canis familiaris

<400> SEQUENCE: 19

Trp Gly Gln Gly Thr Thr Leu Thr Val Ser Ser
1               5                   10

<210> SEQ ID NO 20
<211> LENGTH: 23
<212> TYPE: PRT
<213> ORGANISM: Canis familiaris

<400> SEQUENCE: 20

Asp Ile Val Met Thr Gln Thr Pro Leu Ser Leu Ser Val Ser Pro Gly
1               5                   10                  15

Glu Pro Ala Ser Ile Ser Cys
            20

<210> SEQ ID NO 21
```

```
<211> LENGTH: 23
<212> TYPE: PRT
<213> ORGANISM: Canis familiaris

<400> SEQUENCE: 21

Asp Ile Val Met Thr Gln Thr Pro Leu Ser Leu Ser Val Ser Pro Gly
1               5                   10                  15

Arg Pro Ala Ser Ile Ser Cys
            20

<210> SEQ ID NO 22
<211> LENGTH: 23
<212> TYPE: PRT
<213> ORGANISM: Canis familiaris

<400> SEQUENCE: 22

Asp Ile Val Met Thr Gln Thr Pro Leu Ser Leu Ser Val Ser Pro Gly
1               5                   10                  15

Arg Thr Ala Ser Ile Ser Cys
            20

<210> SEQ ID NO 23
<211> LENGTH: 22
<212> TYPE: PRT
<213> ORGANISM: Canis familiaris

<400> SEQUENCE: 23

Gln Ser Val Leu Thr Gln Pro Ala Ser Val Ser Gly Ser Leu Gly Gln
1               5                   10                  15

Arg Val Thr Ile Ser Cys
            20

<210> SEQ ID NO 24
<211> LENGTH: 27
<212> TYPE: PRT
<213> ORGANISM: Canis familiaris

<400> SEQUENCE: 24

Gln Pro Lys Ala Ser Pro Ser Val Thr Leu Phe Pro Pro Ser Ser Glu
1               5                   10                  15

Glu Leu Gly Ala Asn Lys Ala Thr Leu Val Cys
            20                  25

<210> SEQ ID NO 25
<211> LENGTH: 27
<212> TYPE: PRT
<213> ORGANISM: Canis familiaris

<400> SEQUENCE: 25

Gln Pro Lys Ser Ser Pro Leu Val Thr Leu Phe Pro Pro Ser Ser Glu
1               5                   10                  15

Glu Leu Gly Ala Asn Lys Ala Thr Leu Val Cys
            20                  25

<210> SEQ ID NO 26
<211> LENGTH: 25
<212> TYPE: PRT
<213> ORGANISM: Canis familiaris

<400> SEQUENCE: 26

Glu Val Gln Leu Val Glu Ser Gly Gly Asp Leu Val Lys Pro Gly Gly
1               5                   10                  15

Ser Leu Arg Leu Ser Cys Val Thr Ser
            20                  25
```

<210> SEQ ID NO 27
<211> LENGTH: 25
<212> TYPE: PRT
<213> ORGANISM: Canis familiaris

<400> SEQUENCE: 27

Glu Val Gln Leu Val Glu Ser Gly Gly Asn Leu Val Lys Pro Gly Gly
1               5                   10                  15

Ser Leu Arg Leu Ser Cys Val Ala Ser
            20                  25

<210> SEQ ID NO 28
<211> LENGTH: 25
<212> TYPE: PRT
<213> ORGANISM: Canis familiaris

<400> SEQUENCE: 28

Glu Val Gln Leu Val Glu Ser Gly Gly Asp Leu Glu Lys Pro Gly Gly
1               5                   10                  15

Ser Leu Arg Leu Ser Cys Val Ala Ser
            20                  25

<210> SEQ ID NO 29
<211> LENGTH: 25
<212> TYPE: PRT
<213> ORGANISM: Canis familiaris

<400> SEQUENCE: 29

Glu Val Gln Leu Val Glu Ser Gly Glu Asp Leu Val Lys Pro Gly Gly
1               5                   10                  15

Ser Leu Arg Leu Ser Cys Val Ala Ser
            20                  25

<210> SEQ ID NO 30
<211> LENGTH: 25
<212> TYPE: PRT
<213> ORGANISM: Canis familiaris

<400> SEQUENCE: 30

Glu Val Gln Leu Val Glu Ser Gly Gly Asp Leu Val Lys Pro Ala Gly
1               5                   10                  15

Ser Leu Arg Leu Ser Cys Val Ala Ser
            20                  25

<210> SEQ ID NO 31
<211> LENGTH: 25
<212> TYPE: PRT
<213> ORGANISM: Canis familiaris

<400> SEQUENCE: 31

Glu Val Gln Leu Val Glu Ser Gly Gly Asp Leu Val Lys Pro Glu Arg
1               5                   10                  15

Ser Leu Arg Leu Ser Cys Val Ala Ser
            20                  25

<210> SEQ ID NO 32
<211> LENGTH: 25
<212> TYPE: PRT
<213> ORGANISM: Canis familiaris

<400> SEQUENCE: 32

Glu Val Gln Leu Val Glu Ser Gly Gly Asp Leu Val Lys Pro Glu Gly
1               5                   10                  15

Ser Leu Arg Leu Ser Cys Val Ala Ser
            20                  25

<210> SEQ ID NO 33
<211> LENGTH: 25
<212> TYPE: PRT
<213> ORGANISM: Canis familiaris

<400> SEQUENCE: 33

Glu Val Gln Leu Val Glu Ser Gly Gly Asp Leu Val Lys Pro Gly Gly
1               5                   10                  15

Thr Leu Arg Leu Ser Cys Val Ala Ser
            20                  25

<210> SEQ ID NO 34
<211> LENGTH: 25
<212> TYPE: PRT
<213> ORGANISM: Canis familiaris

<400> SEQUENCE: 34

Glu Glu Gln Leu Val Glu Phe Gly Gly His Met Val Asn Pro Gly Gly
1               5                   10                  15

Ser Leu Gly Leu Ser Cys Gln Ala Ser
            20                  25

<210> SEQ ID NO 35
<211> LENGTH: 25
<212> TYPE: PRT
<213> ORGANISM: Canis familiaris

<400> SEQUENCE: 35

Glu Val Gln Leu Val Glu Ser Gly Gly Asp Leu Ala Lys Pro Gly Gly
1               5                   10                  15

Ser Leu Arg Leu Ser Cys Val Ala Ser
            20                  25

<210> SEQ ID NO 36
<211> LENGTH: 25
<212> TYPE: PRT
<213> ORGANISM: Canis familiaris

<400> SEQUENCE: 36

Glu Val Gln Leu Val Glu Ser Gly Gly Asp Leu Val Lys Pro Glu Gly
1               5                   10                  15

Ser Leu Arg Leu Ser Cys Val Val Ser
            20                  25

<210> SEQ ID NO 37
<211> LENGTH: 25
<212> TYPE: PRT
<213> ORGANISM: Canis familiaris

<400> SEQUENCE: 37

Glu Val Gln Leu Val Gln Ser Gly Ala Glu Val Lys Lys Pro Gly Ala
1               5                   10                  15

Ser Val Lys Val Ser Cys Lys Thr Ser
            20                  25

<210> SEQ ID NO 38
<211> LENGTH: 25
<212> TYPE: PRT

```
<213> ORGANISM: Canis familiaris

<400> SEQUENCE: 38

Glu Val Gln Leu Val Glu Ser Gly Gly Asp Leu Val Lys Pro Gly Gly
1               5                   10                  15

Ser Leu Arg Leu Ser Cys Val Ala Ser
            20                  25

<210> SEQ ID NO 39
<211> LENGTH: 25
<212> TYPE: PRT
<213> ORGANISM: Canis familiaris

<400> SEQUENCE: 39

Glu Val Gln Leu Val Glu Ser Gly Gly Asp Leu Met Lys Pro Gly Gly
1               5                   10                  15

Ser Leu Arg Leu Ser Cys Val Ala Ser
            20                  25

<210> SEQ ID NO 40
<211> LENGTH: 25
<212> TYPE: PRT
<213> ORGANISM: Canis familiaris

<400> SEQUENCE: 40

Glu Val Gln Leu Val Glu Ser Gly Gly Asp Leu Val Lys Pro Gly Gly
1               5                   10                  15

Ser Leu Arg Leu Ser Cys Val Ala Phe
            20                  25

<210> SEQ ID NO 41
<211> LENGTH: 107
<212> TYPE: PRT
<213> ORGANISM: Rattus norvegicus

<400> SEQUENCE: 41

Asp Ile Lys Met Thr Gln Ser Pro Ser Phe Leu Ser Ala Ser Val Gly
1               5                   10                  15

Asp Arg Val Thr Leu Asn Cys Lys Ala Ser Gln Asn Ile Asp Lys Tyr
            20                  25                  30

Leu Asn Trp Tyr Gln Gln Lys Leu Gly Glu Ser Pro Lys Leu Leu Ile
        35                  40                  45

Tyr Asn Thr Asn Asn Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Leu Gln His Ile Ser Arg Pro Arg
                85                  90                  95

Thr Phe Gly Thr Gly Thr Lys Leu Glu Leu Lys
            100                 105

<210> SEQ ID NO 42
<211> LENGTH: 105
<212> TYPE: PRT
<213> ORGANISM: Artificial Sequence
<220> FEATURE:
<223> OTHER INFORMATION: Rattus Norvegicus/Canis Familiaris

<400> SEQUENCE: 42

Gln Ser Val Leu Thr Gln Pro Ala Ser Val Ser Gly Ser Leu Gly Gln
1               5                   10                  15
```

```
Arg Val Thr Ile Ser Cys Lys Ala Ser Gln Asn Ile Asp Lys Tyr Leu
            20                  25                  30

Asn Trp Tyr Gln Gln Lys Leu Gly Glu Ser Pro Lys Leu Leu Ile Tyr
        35                  40                  45

Asn Thr Asn Asn Leu Gln Thr Gly Ile Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Val Ala Thr Tyr Phe Cys Leu Gln His Ile Ser Arg Pro Arg Thr
                85                  90                  95

Phe Gly Gly Gly Thr His Leu Thr Val
            100                 105

<210> SEQ ID NO 43
<211> LENGTH: 107
<212> TYPE: PRT
<213> ORGANISM: Artificial Sequence
<220> FEATURE:
<223> OTHER INFORMATION: rattus norvegicus/canis familiaris

<400> SEQUENCE: 43

Asp Ile Lys Met Thr Gln Ser Pro Ser Phe Leu Ser Ala Ser Val Gly
1               5                   10                  15

Asp Arg Val Thr Leu Asn Cys Lys Ala Ser Gln Asn Ile Asp Lys Tyr
            20                  25                  30

Leu Asn Trp Tyr Gln Gln Lys Leu Gly Glu Ser Pro Lys Leu Leu Ile
        35                  40                  45

Tyr Asn Thr Asn Asn Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Leu Gln His Ile Ser Arg Pro Arg
                85                  90                  95

Thr Phe Gly Gly Gly Thr His Leu Thr Val Leu
            100                 105

<210> SEQ ID NO 44
<211> LENGTH: 121
<212> TYPE: PRT
<213> ORGANISM: Rattus norvegicus

<400> SEQUENCE: 44

Glu Val Lys Leu Leu Glu Ser Gly Gly Gly Leu Val Gln Pro Gly Gly
1               5                   10                  15

Ser Met Arg Leu Ser Cys Ala Gly Ser Gly Phe Thr Phe Thr Asp Phe
            20                  25                  30

Tyr Met Asn Trp Ile Arg Gln Pro Ala Gly Lys Ala Pro Glu Trp Leu
        35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Thr Gln Asn Met
65                  70                  75                  80

Leu Tyr Leu Gln Met Asn Thr Leu Arg Ala Glu Asp Thr Ala Thr Tyr
                85                  90                  95

Tyr Cys Ala Arg Glu Gly His Thr Ala Ala Pro Phe Asp Tyr Trp Gly
            100                 105                 110

Gln Gly Val Met Val Thr Val Ser Ser
        115                 120
```

<210> SEQ ID NO 45
<211> LENGTH: 121
<212> TYPE: PRT
<213> ORGANISM: Artificial Sequence
<220> FEATURE:
<223> OTHER INFORMATION: Rattus norvegicus/Canis familiaris

<400> SEQUENCE: 45

```
Glu Val Gln Leu Val Glu Ser Gly Gly Asp Leu Val Lys Pro Gly Gly
1               5                   10                  15
Ser Leu Arg Leu Ser Cys Ala Gly Ser Gly Phe Thr Phe Thr Asp Phe
            20                  25                  30
Tyr Met Asn Trp Ile Arg Gln Pro Ala Gly Lys Ala Pro Glu Trp Leu
        35                  40                  45
Gly Phe Ile Arg Asp Lys Ala Lys Gly Tyr Thr Thr Glu Tyr Asn Pro
    50                  55                  60
Ser Val Lys Gly Arg Phe Thr Ile Ser Arg Asp Asn Thr Gln Asn Met
65                  70                  75                  80
Leu Tyr Leu Gln Met Asn Thr Leu Arg Ala Glu Asp Thr Ala Thr Tyr
                85                  90                  95
Tyr Cys Ala Arg Glu Gly His Thr Ala Ala Pro Phe Asp Tyr Trp Gly
            100                 105                 110
Gln Gly Thr Leu Val Thr Val Ser Ser
        115                 120
```

<210> SEQ ID NO 46
<211> LENGTH: 121
<212> TYPE: PRT
<213> ORGANISM: Artificial Sequence
<220> FEATURE:
<223> OTHER INFORMATION: Rattus norvegicus/Canis familiaris

<400> SEQUENCE: 46

```
Glu Val Lys Leu Leu Glu Ser Gly Gly Gly Leu Val Gln Pro Gly Gly
1               5                   10                  15
Ser Met Arg Leu Ser Cys Ala Gly Ser Gly Phe Thr Phe Thr Asp Phe
            20                  25                  30
Tyr Met Asn Trp Ile Arg Gln Pro Ala Gly Lys Ala Pro Glu Trp Leu
        35                  40                  45
Gly Phe Ile Arg Asp Lys Ala Lys Gly Tyr Thr Thr Glu Tyr Asn Pro
    50                  55                  60
Ser Val Lys Gly Arg Phe Thr Ile Ser Arg Asp Asn Thr Gln Asn Met
65                  70                  75                  80
Leu Tyr Leu Gln Met Asn Thr Leu Arg Ala Glu Asp Thr Ala Thr Tyr
                85                  90                  95
Tyr Cys Ala Arg Glu Gly His Thr Ala Ala Pro Phe Asp Tyr Trp Gly
            100                 105                 110
Gln Gly Thr Leu Val Thr Val Ser Ser
        115                 120
```

<210> SEQ ID NO 47
<211> LENGTH: 118
<212> TYPE: PRT
<213> ORGANISM: Mus musculus

<400> SEQUENCE: 47

```
Glu Val Lys Leu Val Glu Ser Gly Gly Gly Leu Val Gln Pro Gly Gly
1               5                   10                  15
```

```
Ser Leu Lys Leu Ser Cys Ala Thr Ser Gly Phe Thr Phe Ser Asp Tyr
             20                  25                  30

Tyr Met Tyr Trp Val Arg Gln Thr Pro Glu Lys Arg Leu Glu Trp Val
         35                  40                  45

Ala Tyr Ile Ser Asn Gly Gly Ser Thr Tyr Tyr Pro Asp Thr Val
 50                  55                  60

Lys Gly Arg Phe Thr Ile Ser Arg Asp Asn Ala Lys Asn Thr Leu Tyr
 65                  70                  75                  80

Leu Gln Met Ser Arg Leu Lys Ser Glu Asp Thr Ala Met Tyr Tyr Cys
             85                  90                  95

Ala Arg His Gly Gly Tyr Tyr Ala Met Asp Tyr Trp Gly Gln Gly Thr
            100                 105                 110

Ser Val Thr Val Ser Ser
            115

<210> SEQ ID NO 48
<211> LENGTH: 107
<212> TYPE: PRT
<213> ORGANISM: Mus musculus

<400> SEQUENCE: 48

Asp Ile Gln Met Asn Gln Ser Pro Ser Ser Leu Ser Ala Ser Leu Gly
1               5                  10                  15

Asp Thr Ile Thr Ile Thr Cys His Ala Ser Gln Asn Ile Asn Val Trp
             20                  25                  30

Leu Ser Trp Tyr Gln Gln Lys Pro Gly Asn Ile Pro Lys Leu Leu Ile
         35                  40                  45

Tyr Lys Ala Ser Asn Leu His Thr Gly Val Pro Ser Arg Phe Ser Gly
 50                  55                  60

Ser Gly Ser Gly Thr Gly Phe Thr Leu Thr Ile Ser Ser Leu Gln Pro
 65                  70                  75                  80

Glu Asp Ile Ala Thr Tyr Tyr Cys Gln Gln Gly Gln Ser Tyr Pro Leu
             85                  90                  95

Thr Phe Gly Gly Gly Thr Lys Leu Glu Ile Lys
            100                 105

<210> SEQ ID NO 49
<211> LENGTH: 213
<212> TYPE: PRT
<213> ORGANISM: Artificial Sequence
<220> FEATURE:
<223> OTHER INFORMATION: Mus musculus/Canis familiaris

<400> SEQUENCE: 49

Asp Ile Gln Met Asn Gln Ser Pro Ser Ser Leu Ser Ala Ser Leu Gly
1               5                  10                  15

Asp Thr Ile Thr Ile Thr Cys His Ala Ser Gln Asn Ile Asn Val Trp
             20                  25                  30

Leu Ser Trp Tyr Gln Gln Lys Pro Gly Asn Ile Pro Lys Leu Leu Ile
         35                  40                  45

Tyr Lys Ala Ser Asn Leu His Thr Gly Val Pro Ser Arg Phe Ser Gly
 50                  55                  60

Ser Gly Ser Gly Thr Gly Phe Thr Leu Thr Ile Ser Ser Leu Gln Pro
 65                  70                  75                  80

Glu Asp Ile Ala Thr Tyr Tyr Cys Gln Gln Gly Gln Ser Tyr Pro Leu
             85                  90                  95

Thr Phe Gly Gly Gly Thr Lys Leu Glu Ile Lys Gly Gln Pro Lys Ala
            100                 105                 110
```

```
Ser Pro Ser Val Thr Leu Phe Pro Pro Ser Glu Glu Leu Gly Ala
    115                 120                 125

Asn Lys Ala Thr Leu Val Cys Leu Ile Ser Asp Phe Tyr Pro Ser Gly
130                 135                 140

Val Thr Val Ala Trp Lys Ala Asp Gly Ser Pro Ile Thr Gln Gly Val
145                 150                 155                 160

Glu Thr Thr Lys Pro Ser Lys Gln Ser Asn Asn Lys Tyr Ala Ala Ser
                165                 170                 175

Ser Tyr Leu Ser Leu Thr Pro Asp Lys Trp Lys Ser His Ser Ser Phe
            180                 185                 190

Ser Cys Leu Val Thr His Glu Gly Ser Thr Val Glu Lys Lys Val Ala
        195                 200                 205

Pro Ala Glu Cys Ser
    210

<210> SEQ ID NO 50
<211> LENGTH: 216
<212> TYPE: PRT
<213> ORGANISM: Artificial Sequence
<220> FEATURE:
<223> OTHER INFORMATION: Mus muscululs/Canis familiaris

<400> SEQUENCE: 50

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Gly Gly Thr Lys Leu Glu Ile Lys Asn Asp Ala Gln Pro
            100                 105                 110

Ala Val Tyr Leu Phe Gln Pro Ser Pro Asp Gln Leu His Thr Gly Ser
        115                 120                 125

Ala Ser Val Val Cys Leu Leu Asn Ser Phe Tyr Pro Lys Asp Ile Asn
    130                 135                 140

Val Lys Trp Lys Val Asp Gly Val Ile Gln Asp Thr Gly Ile Gln Glu
145                 150                 155                 160

Ser Val Thr Glu Gln Asp Lys Asp Ser Thr Tyr Ser Leu Ser Ser Thr
                165                 170                 175

Leu Thr Met Ser Ser Thr Glu Tyr Leu Ser His Glu Leu Tyr Ser Cys
            180                 185                 190

Glu Ile Thr His Lys Ser Leu Pro Ser Thr Leu Ile Lys Ser Phe Gln
        195                 200                 205

Arg Ser Glu Cys Gln Arg Val Asp
    210                 215

<210> SEQ ID NO 51
<211> LENGTH: 107
<212> TYPE: PRT
<213> ORGANISM: Artificial Sequence
<220> FEATURE:
```

<223> OTHER INFORMATION: Mus musculus/Canis familiaris

<400> SEQUENCE: 51

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Gly Gly Thr His Leu Thr Val Leu
            100                 105

<210> SEQ ID NO 52
<211> LENGTH: 118
<212> TYPE: PRT
<213> ORGANISM: Artificial Sequence
<220> FEATURE:
<223> OTHER INFORMATION: Mus musculus/Canis familiaris

<400> SEQUENCE: 52

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Gly Gly Gly Ser Thr Tyr Tyr Pro Asp Thr Val
50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg His Gly Gly Tyr Tyr Ala Met Asp Tyr Trp Gly Gln Gly Thr
            100                 105                 110

Leu Val Thr Val Ser Ser
        115

<210> SEQ ID NO 53
<211> LENGTH: 118
<212> TYPE: PRT
<213> ORGANISM: Artificial Sequence
<220> FEATURE:
<223> OTHER INFORMATION: Mus musculus/Canis familiaris

<400> SEQUENCE: 53

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Gly Gly Gly Ser Thr Tyr Tyr Pro Asp Thr Val
50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
            85                  90                  95

Ala Arg His Gly Gly Tyr Tyr Ala Met Asp Tyr Trp Gly Gln Gly Thr
        100                 105                 110

Ser Val Thr Val Ser Ser
        115

<210> SEQ ID NO 54
<211> LENGTH: 335
<212> TYPE: PRT
<213> ORGANISM: Canis familiaris

<400> SEQUENCE: 54

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Met Leu Gly Gly Pro Ser Val Phe Ile
        115                 120                 125

Phe Pro Pro Lys Pro Lys Asp Thr Leu Leu Ile Ala Arg Thr Pro Glu
    130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
        195                 200                 205

Val Asn Asn Lys Ala Leu Pro Ser Pro Ile Glu Arg Thr Ile Ser Lys
    210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
        275                 280                 285

Asp Gly Ser Tyr Phe Leu Tyr Ser Lys Leu Ser Val Asp Lys Ser Arg
    290                 295                 300

Trp Gln Arg Gly Asp Thr Phe Ile Cys Ala Val Met His Glu Ala Leu
305                 310                 315                 320

```
His Asn His Tyr Thr Gln Lys Ser Leu Ser His Ser Pro Gly Lys
                325                 330                 335

<210> SEQ ID NO 55
<211> LENGTH: 106
<212> TYPE: PRT
<213> ORGANISM: Canis familiaris

<400> SEQUENCE: 55

Gly Gln Pro Lys Ala Ser Pro Ser Val Thr Leu Phe Pro Pro Ser Ser
1               5                   10                  15

Glu Glu Leu Gly Ala Asn Lys Ala Thr Leu Val Cys Leu Ile Ser Asp
            20                  25                  30

Phe Tyr Pro Ser Gly Val Thr Val Ala Trp Lys Ala Asp Gly Ser Pro
        35                  40                  45

Ile Thr Gln Gly Val Glu Thr Thr Lys Pro Ser Lys Gln Ser Asn Asn
    50                  55                  60

Lys Tyr Ala Ala Ser Ser Tyr Leu Ser Leu Thr Pro Asp Lys Trp Lys
65                  70                  75                  80

Ser His Ser Ser Phe Ser Cys Leu Val Thr His Glu Gly Ser Thr Val
                85                  90                  95

Glu Lys Lys Val Ala Pro Ala Glu Cys Ser
            100                 105

<210> SEQ ID NO 56
<211> LENGTH: 109
<212> TYPE: PRT
<213> ORGANISM: Canis familiaris

<400> SEQUENCE: 56

Asn Asp Ala Gln Pro Ala Val Tyr Leu Phe Gln Pro Ser Pro Asp Gln
1               5                   10                  15

Leu His Thr Gly Ser Ala Ser Val Val Cys Leu Leu Asn Ser Phe Tyr
            20                  25                  30

Pro Lys Asp Ile Asn Val Lys Trp Lys Val Asp Gly Val Ile Gln Asp
        35                  40                  45

Thr Gly Ile Gln Glu Ser Val Thr Glu Gln Asp Lys Asp Ser Thr Tyr
    50                  55                  60

Ser Leu Ser Ser Thr Leu Thr Met Ser Ser Thr Glu Tyr Leu Ser His
65                  70                  75                  80

Glu Leu Tyr Ser Cys Glu Ile Thr His Lys Ser Leu Pro Ser Thr Leu
                85                  90                  95

Ile Lys Ser Phe Gln Arg Ser Glu Cys Gln Arg Val Asp
            100                 105

<210> SEQ ID NO 57
<211> LENGTH: 17
<212> TYPE: DNA
<213> ORGANISM: Canis familiaris

<400> SEQUENCE: 57
gcctccacca cggcccc                                                        17

<210> SEQ ID NO 58
<211> LENGTH: 20
<212> TYPE: DNA
<213> ORGANISM: Canis familiaris

<400> SEQUENCE: 58
```

```
tcatttaccc ggagaatggg                                              20

<210> SEQ ID NO 59
<211> LENGTH: 19
<212> TYPE: DNA
<213> ORGANISM: Canis familiaris

<400> SEQUENCE: 59
ggtcagccca aggccwmcc                                               19

<210> SEQ ID NO 60
<211> LENGTH: 19
<212> TYPE: DNA
<213> ORGANISM: Canis familiaris

<400> SEQUENCE: 60
ctaagagcac tctgcrggg                                               19

<210> SEQ ID NO 61
<211> LENGTH: 19
<212> TYPE: DNA
<213> ORGANISM: Canis familiaris

<400> SEQUENCE: 61
aatgatgccc agccagccg                                               19

<210> SEQ ID NO 62
<211> LENGTH: 21
<212> TYPE: DNA
<213> ORGANISM: Canis familiaris

<400> SEQUENCE: 62
ttagtccact ctctgacact c                                            21

<210> SEQ ID NO 63
<211> LENGTH: 21
<212> TYPE: DNA
<213> ORGANISM: Canis familiaris

<400> SEQUENCE: 63
tgagatgaca cacccagaa a                                             21

<210> SEQ ID NO 64
<211> LENGTH: 21
<212> TYPE: DNA
<213> ORGANISM: Canis familiaris

<400> SEQUENCE: 64
ttaagggatg ctgtcgtttt c                                            21

<210> SEQ ID NO 65
<211> LENGTH: 25
<212> TYPE: DNA
<213> ORGANISM: Canis familiaris

<400> SEQUENCE: 65
aatattacca tttcccattt tttta                                        25

<210> SEQ ID NO 66
<211> LENGTH: 23
<212> TYPE: DNA
<213> ORGANISM: Canis familiaris

<400> SEQUENCE: 66
```

-continued tatgctgcca caatattgta tag                                    23

<210> SEQ ID NO 67
<211> LENGTH: 297
<212> TYPE: PRT
<213> ORGANISM: Canis familiaris

<400> SEQUENCE: 67

Met Thr Thr Pro Arg Asn Ser Met Ser Gly Thr Leu Pro Val Asp Pro
1               5                   10                  15

Met Lys Ser Pro Thr Ala Met Tyr Pro Val Gln Lys Ile Ile Pro Lys
            20                  25                  30

Arg Met Pro Ser Val Val Gly Pro Thr Gln Asn Phe Phe Met Arg Glu
        35                  40                  45

Ser Lys Thr Leu Gly Ala Val Gln Ile Met Asn Gly Leu Phe His Ile
    50                  55                  60

Ala Leu Gly Ser Leu Leu Met Ile His Thr Asp Val Tyr Ala Pro Ile
65                  70                  75                  80

Cys Ile Thr Met Trp Tyr Pro Leu Trp Gly Gly Ile Met Phe Ile Ile
                85                  90                  95

Ser Gly Ser Leu Leu Ala Ala Asp Lys Asn Pro Arg Lys Ser Leu
            100                 105                 110

Val Lys Gly Lys Met Ile Met Asn Ser Leu Ser Leu Phe Ala Ala Ile
        115                 120                 125

Ser Gly Ile Ile Phe Leu Ile Met Asp Ile Phe Asn Ile Thr Ile Ser
    130                 135                 140

His Phe Phe Lys Met Glu Asn Leu Asn Leu Ile Lys Ala Pro Met Pro
145                 150                 155                 160

Tyr Val Asp Ile His Asn Cys Asp Pro Ala Asn Pro Ser Glu Lys Asn
                165                 170                 175

Ser Leu Ser Ile Gln Tyr Cys Gly Ser Ile Arg Ser Val Phe Leu Gly
            180                 185                 190

Val Phe Ala Val Met Val Ile Phe Thr Phe Phe Gln Lys Leu Val Thr
        195                 200                 205

Ala Gly Ile Val Glu Asn Glu Trp Lys Lys Leu Cys Ser Lys Pro Lys
    210                 215                 220

Ser Asp Val Val Val Leu Leu Ala Ala Glu Lys Lys Glu Gln Pro
225                 230                 235                 240

Ile Glu Thr Thr Glu Glu Met Val Glu Leu Thr Glu Ile Ala Ser Gln
                245                 250                 255

Pro Lys Lys Glu Glu Asp Ile Glu Ile Ile Pro Val Gln Glu Glu Glu
            260                 265                 270

Glu Glu Leu Glu Ile Asn Phe Ala Glu Pro Pro Gln Gln Glu Ser
        275                 280                 285

Ser Pro Ile Glu Asn Asp Ser Ile Pro
    290                 295

<210> SEQ ID NO 68
<211> LENGTH: 26
<212> TYPE: PRT
<213> ORGANISM: Felis catus

<400> SEQUENCE: 68

Gly Gly Ala Thr Cys Cys Thr Ala Ala Gly Gly Ala Ala Thr Gly
1               5                   10                  15

Cys Thr Ala Thr Cys Gly Thr Thr Thr
            20                  25

<210> SEQ ID NO 69
<211> LENGTH: 298
<212> TYPE: PRT
<213> ORGANISM: Felis catus

<400> SEQUENCE: 69

Met Thr Thr Pro Arg Asn Ser Met Ser Gly Thr Leu Pro Ala Asp Ala
1               5                   10                  15

Met Lys Ser Pro Thr Ala Met Asn Pro Val Gln Lys Ile Ile Pro Lys
            20                  25                  30

Lys Met Pro Ser Val Val Gly Pro Thr Gln Asn Phe Phe Met Lys Glu
        35                  40                  45

Ser Lys Pro Leu Gly Ala Val Gln Ile Met Asn Gly Leu Phe His Met
    50                  55                  60

Ala Leu Gly Gly Leu Leu Met Ile His Met Glu Val Tyr Ala Pro Ile
65                  70                  75                  80

Cys Met Thr Val Trp Tyr Pro Leu Trp Gly Ile Met Tyr Ile Ile
                85                  90                  95

Ser Gly Ser Leu Leu Val Ala Ala Glu Lys Asn Pro Arg Lys Ser Leu
            100                 105                 110

Val Lys Gly Lys Met Ile Met Asn Ser Leu Ser Leu Phe Ala Ala Ile
        115                 120                 125

Ser Gly Met Ile Leu Leu Ile Met Asp Ile Phe Asn Ile Ala Ile Ser
    130                 135                 140

His Phe Phe Lys Met Glu Asn Leu Asn Leu Leu Lys Ser Pro Lys Pro
145                 150                 155                 160

Tyr Ile Asp Ile His Thr Cys Gln Pro Glu Ser Lys Pro Ser Glu Lys
                165                 170                 175

Asn Ser Leu Ser Ile Lys Tyr Cys Asp Ser Ile Arg Ser Val Phe Leu
            180                 185                 190

Ser Ile Phe Ala Val Met Val Val Phe Thr Leu Phe Gln Lys Leu Val
        195                 200                 205

Thr Ala Gly Ile Val Glu Asn Glu Trp Lys Lys Leu Cys Ser Lys Pro
    210                 215                 220

Lys Ala Asp Val Val Val Leu Leu Ala Ala Glu Glu Lys Lys Glu Gln
225                 230                 235                 240

Leu Val Glu Ile Thr Glu Glu Ala Val Glu Leu Thr Glu Val Ser Ser
                245                 250                 255

Gln Pro Lys Asn Glu Glu Asp Ile Glu Ile Pro Val Gln Glu Glu
            260                 265                 270

Glu Glu Glu Thr Glu Met Asn Phe Pro Glu Pro Pro Gln Asp Gln Glu
        275                 280                 285

Pro Ser Leu Ile Glu Asn Asp Ser Ile Pro
    290                 295

<210> SEQ ID NO 70
<211> LENGTH: 40
<212> TYPE: DNA
<213> ORGANISM: Canis familiaris

<400> SEQUENCE: 70
caacaaagct tgccgccacc atgaagggct tcctcttcct                          40

<210> SEQ ID NO 71
<211> LENGTH: 31
<212> TYPE: DNA

```
<213> ORGANISM: Canis familiaris

<400> SEQUENCE: 71
caacaggatc ctcagctgag gtagaagagc t                            31

<210> SEQ ID NO 72
<211> LENGTH: 67
<212> TYPE: PRT
<213> ORGANISM: Canis familiaris

<400> SEQUENCE: 72

Met Lys Gly Phe Leu Phe Leu Leu Thr Ile Ser Leu Leu Val Met
1               5                   10                  15

Ile Gln Ile Gln Thr Gly Val Leu Gly Asn Ser Thr Thr Pro Arg Met
            20                  25                  30

Thr Thr Lys Lys Val Lys Ser Ala Thr Pro Ala Leu Ser Ser Leu Gly
        35                  40                  45

Gly Gly Ser Val Leu Leu Phe Leu Ala Asn Thr Leu Ile Gln Leu Phe
    50                  55                  60

Tyr Leu Ser
65

<210> SEQ ID NO 73
<211> LENGTH: 67
<212> TYPE: PRT
<213> ORGANISM: Felis catus

<400> SEQUENCE: 73

Met Lys Gly Phe Leu Phe Leu Leu Thr Ile Ser Leu Leu Val Met
1               5                   10                  15

Ile Gln Ile Gln Thr Gly Val Leu Gly Asn Thr Thr Thr Ala Ala Thr
            20                  25                  30

Thr Thr Lys Lys Pro Lys Ser Ala Thr Pro Pro Leu Ser Ser Leu Ser
        35                  40                  45

Ser Gly Ser Val Leu Leu Phe Leu Ala Asn Ile Leu Val Gln Leu Phe
    50                  55                  60

Tyr Leu Ser
65

<210> SEQ ID NO 74
<211> LENGTH: 8
<212> TYPE: PRT
<213> ORGANISM: Canis familiaris

<400> SEQUENCE: 74

Thr Asp Val Tyr Ala Pro Ile Cys
1               5

<210> SEQ ID NO 75
<211> LENGTH: 48
<212> TYPE: PRT
<213> ORGANISM: Canis familiaris

<400> SEQUENCE: 75

Asn Ile Thr Ile Ser His Phe Phe Lys Met Glu Asn Leu Asn Leu Ile
1               5                   10                  15

Lys Ala Pro Met Pro Tyr Val Asp Ile His Asn Cys Asp Pro Ala Asn
            20                  25                  30

Pro Ser Glu Lys Asn Ser Leu Ser Ile Gln Tyr Cys Gly Ser Ile Arg
        35                  40                  45
```

<210> SEQ ID NO 76
<211> LENGTH: 11
<212> TYPE: PRT
<213> ORGANISM: Canis familiaris

<400> SEQUENCE: 76

His Thr Asp Val Tyr Ala Pro Ile Cys Ile Thr
1               5                   10

<210> SEQ ID NO 77
<211> LENGTH: 11
<212> TYPE: PRT
<213> ORGANISM: Canis familiaris

<400> SEQUENCE: 77

Leu Ser Ile Gln Tyr Cys Gly Ser Ile Arg Ser
1               5                   10

<210> SEQ ID NO 78
<211> LENGTH: 17
<212> TYPE: PRT
<213> ORGANISM: Canis familiaris

<400> SEQUENCE: 78

Leu Ile Lys Ala Pro Met Pro Tyr Val Asp Ile His Asn Cys Asp Pro
1               5                   10                  15

Ala

<210> SEQ ID NO 79
<211> LENGTH: 7
<212> TYPE: PRT
<213> ORGANISM: Canis familiaris

<400> SEQUENCE: 79

Asn Ile Thr Ile Ser His Phe
1               5

<210> SEQ ID NO 80
<211> LENGTH: 12
<212> TYPE: PRT
<213> ORGANISM: Canis familiaris

<400> SEQUENCE: 80

Val Asp Ile His Asn Cys Asp Pro Ala Asn Pro Ser
1               5                   10

<210> SEQ ID NO 81
<211> LENGTH: 12
<212> TYPE: PRT
<213> ORGANISM: Canis familiaris

<400> SEQUENCE: 81

Lys Met Glu Asn Leu Asn Leu Ile Lys Ala Pro Met
1               5                   10

<210> SEQ ID NO 82
<211> LENGTH: 12
<212> TYPE: PRT
<213> ORGANISM: Canis familiaris

<400> SEQUENCE: 82

Thr Ile Ser His Phe Phe Lys Met Glu Asn Leu Asn
1               5                   10

```
<210> SEQ ID NO 83
<211> LENGTH: 12
<212> TYPE: PRT
<213> ORGANISM: Canis familiaris

<400> SEQUENCE: 83

Pro Met Pro Tyr Val Asp Ile His Asn Cys Asp Pro
1               5                   10

<210> SEQ ID NO 84
<211> LENGTH: 12
<212> TYPE: PRT
<213> ORGANISM: Canis familiaris

<400> SEQUENCE: 84

Asn Cys Asp Pro Ala Asn Pro Ser Glu Lys Asn Ser
1               5                   10

<210> SEQ ID NO 85
<211> LENGTH: 16
<212> TYPE: PRT
<213> ORGANISM: Canis familiaris

<400> SEQUENCE: 85

Tyr Val Asp Ile His Asn Cys Asp Pro Ala Asn Pro Ser Glu Lys Asn
1               5                   10                  15

<210> SEQ ID NO 86
<211> LENGTH: 16
<212> TYPE: PRT
<213> ORGANISM: Canis familiaris

<400> SEQUENCE: 86

Gly Gly Ser Val Leu Leu Phe Leu Ala Asn Thr Leu Ile Gln Leu Phe
1               5                   10                  15

<210> SEQ ID NO 87
<211> LENGTH: 15
<212> TYPE: PRT
<213> ORGANISM: Canis familiaris

<400> SEQUENCE: 87

Phe Leu Phe Leu Leu Leu Thr Ile Ser Leu Leu Val Met Ile Gln
1               5                   10                  15

<210> SEQ ID NO 88
<211> LENGTH: 7
<212> TYPE: PRT
<213> ORGANISM: Canis familiaris

<400> SEQUENCE: 88

Gln Thr Gly Val Leu Gly Asn
1               5

<210> SEQ ID NO 89
<211> LENGTH: 12
<212> TYPE: PRT
<213> ORGANISM: Canis familiaris

<400> SEQUENCE: 89

Lys Val Lys Ser Ala Thr Pro Ala Leu Ser Ser Leu
1               5                   10

<210> SEQ ID NO 90
<211> LENGTH: 10
<212> TYPE: PRT
```

```
<213> ORGANISM: Canis familiaris

<400> SEQUENCE: 90

Pro Arg Met Thr Thr Lys Lys Val Lys Ser
1               5                   10
```

MONOCLONAL ANTIBODIES

RELATED APPLICATIONS

This application claims the benefit of U.S. Provisional Application Ser. No. 61/094,333 filed Sep. 4, 2008 and U.S. Provisional Application Ser. No. 61/163,188 filed Mar. 25, 2009, the entire disclosures of which are incorporated herein by reference.

FIELD OF THE INVENTION

This invention generally relates to monoclonal antibodies for the treatment of diseases, e.g., in mammals and particularly in companion animals, such as dogs, cats and horses. More particularly, the invention provides "heterochimeric" antibody constructs, and antibodies encoded by the constructs, which react with targets useful for detection of targets, diagnosis of disease and treatment of companion animals.

BACKGROUND OF THE INVENTION

The use of antibodies as therapeutic treatment for a variety of diseases and disorders are rapidly increasing because they have shown to be safe and efficacious therapeutic agents. Approved therapeutic monoclonal antibodies for human use include Trastuzumab (antigen: HER2/neu), Edrecolomab (antigen: Ep-CAM), Anti-human milk fat globules (HMFG1) (antigen: HMW Mucin), Cetuximab (antigens: EGF receptor), Alemtuzumab (antigen: CD52), and Rituximab (antigen: CD20). Additional monoclonal antibodies are in various phases of clinical development for humans for a variety of diseases with the majority targeting various forms of cancer.

Antibodies target an antigen through its binding of a specific epitope on an antigen by the interaction with the variable region of the antibody molecule. Furthermore, antibodies have the ability to mediate and/or initiate a variety of biological activities. For example, antibodies can modulate receptor-ligand interactions as agonists or antagonists. Antibody binding can initiate intracellular signalling to stimulate cell growth, cytokine production, or apoptosis. Antibodies can deliver agents bound to the Fc region to specific sites. Antibodies also elicit antibody-mediated cytotoxicity (ADCC), complement-mediated cytotoxicity (CDC), and phagocytosis.

While the properties of antibodies make them very attractive therapeutic agents, there are a number of limitations. There are several methods being utilized to generate antibodies including hybridoma technology, ribosome display, bacterial and yeast display, and others known in the art. The vast majority of monoclonal antibodies (mAbs) are of rodent origin. When such antibodies are administered in a different species, patients can mount their own antibody response to such xenogenic antibodies. Such response may result in the eventual neutralization and elimination of the antibody. One solution to this challenge involves the process of engineering an antibody with sequences compatible with the species subjected to the treatment. This process can prevent or greatly delay the patient developing an immune response against the administered therapeutic monoclonal antibody and extends the half-life of that antibody in the circulation of the treated subject. Such approaches, however, require careful balancing so that the antibody retains specificity and binding.

These limitations have prompted the development of engineering technologies known as "humanization". Humanized antibodies can be generated as chimeric antibodies or fragments thereof which contain minimal sequence derived from non-human immunoglobulin. For the most part, humanized antibodies are human antibodies (i.e. "recipient antibody" or "target species antibody") in which residues from a complementarity determining region (CDR) of the recipient are replaced by residues from a CDR of a non-human species (i.e. "donor antibody" or "originating species antibody") such as mouse, having the desired properties such as specificity, affinity, and potency. In some instances, framework region (FR) residues of the human immunoglobulin are replaced by corresponding non-human residues. This humanization strategy is referred to as "CDR grafting" as reported for the making of humanized antibodies (Winter, U.S. Pat. No. 5,225,539). Back mutation of selected target framework residues to the corresponding donor residues might be required to restore and/or improved affinity. Structure-based methods may also be employed for humanization and affinity maturation, for example as described for humanization in U.S. patent application Ser. No. 10/153,159 and related applications. Comparison of the essential framework residues required in humanization of several antibodies, as well as computer modeling based on antibody crystal structures revealed a set of framework residues termed as "Vernier zone residues" (Foote, J. *Mol. Biol.* 224:487-499 (1992)). In addition, several residues in the VH-VL interface zone have been suggested to be important in maintaining affinity for the antigen (Santos, *Prog Nucleic Acid Res Mol. Biol.* 60:169-94 (1998); Kettleborough, et al., *Protein Engin.,* 4:773-783 (1991)). Similar strategies for "caninization" of antibodies for use in dogs are described in WO 03/060080.

Alternatively, humanized antibodies may contain the CDRs from a non-human sequence grafted into pools (e.g. libraries) of individual human framework regions. This newly engineered antibody is able to bind to the same antigen as the original antibody. The antibody constant region is derived from a human antibody. The methodology for performing this aspect is generally described as framework shuffling (Dall'Acqua, *Methods,* 36:43-60 (2005)). Furthermore, the humanized antibody may contain sequences from two or more framework regions derived from at least two human antibody germline sequences with high homology to the donor species. Antibodies designed using this method are described as hybrid antibodies (Rother et al., U.S. Pat. No. 7,393,648).

The approaches described above utilize essentially entire framework regions from one or more antibody variable heavy chains or variable light chains of the target species which are engineered to receive CDRs from the donor species. In some cases, back mutation of selected residues in the variable region is used to enhance presentation of the CDRs. Designing antibodies that minimize immunogenic reaction in a subject to non-native sequences in the antibody, while at the same time preserving antigen binding regions of the antibody sufficiently to maintain efficacy, has proven challenging.

Another challenge for developing therapeutic antibodies targeting proteins is that epitopes on the homologous protein in a different species are frequently different, and the potential for cross-reactivity with other proteins is also different. As a consequence, antibodies have to be made, tested and developed for the specific target in the particular species to be treated.

SUMMARY OF THE INVENTION

The invention provides heterochimeric antibodies and/or fragments thereof comprising (i) Hypervariable region sequences wholly or substantially corresponding to sequences found in antibodies from a donor species; (ii) constant region sequences wholly or substantially corresponding to sequences found in antibodies from a target species which is different from the donor species; and (iii) heavy and/or light chain variable framework sequences which contain at least three, e.g. at least four, or at least five, or at least six contiguous non-CDR residues corresponding to sequences found in antibodies from a target species and at least three, e.g. at least four, or at least five, or at least six contiguous non-CDR residues corresponding to sequences found in antibodies from a donor species. Heterochimeric antibodies as described herein include heterochimeric hybrid antibodies wherein the target antibody sequences are from different antibodies from the target species. In one embodiment, the heterochimeric antibody comprises FR1 and/or FR4 variable region sequences wholly or substantially corresponding to FR1 and/or FR4 variable region sequences found in antibodies from a target species, and CDR, FR2 and FR3 sequences wholly or substantially corresponding to sequences found in the donor species antibody. Methods of making and using these antibodies and fragments are also provided.

In another embodiment the invention provides therapeutic antibodies useful for veterinary application, particularly antibodies directed to canine or feline or equine CD20, CD52, HER2/neu, or IL-6, IL-6 receptor, for example canine CD20 or canine CD52, together with methods of making such antibodies using optimized immunogenic constructs and methods treatment using such antibodies.

DETAILED DESCRIPTION OF THE INVENTION

It is to be understood that both the foregoing general description and the following detailed description are exemplary and explanatory only and are not restrictive of the invention, as claimed. It must be noted that, as used herein and in the appended claims, the singular forms include plural referents; the use of "or" means "and/or" unless stated otherwise. Thus, for example, reference to "a subject polypeptide" includes a plurality of such polypeptides and reference to "the agent" includes reference to one or more agents and equivalents thereof known to those skilled in the art, and so forth. Moreover, it must be understood that the invention is not limited to the particular embodiments described, as such may, of course, vary. Further, the terminology used to describe particular embodiments is not intended to be limiting, since the scope of the present invention will be limited only by its claims.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Unless otherwise defined, all technical and scientific terms used herein have the same meaning as commonly understood by one of ordinary skill in the art to which this invention belongs. Suitable methods and materials are described below, however methods and materials similar or equivalent to those described herein can be used in the practice of the present invention. Thus, the materials, methods, and examples are illustrative only and not intended to be limiting. All publications, patent applications, patents, and other references mentioned herein are incorporated by reference in their entirety. In case of conflict, the present specification, including definitions, will control.

Standard techniques may be used for recombinant DNA, oligonucleotide synthesis, tissue culture and transfection (e.g., electroporation, lipofection, etc.). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)).

The present invention provides methods for engineering heterochimeric antibodies and/or fragments thereof suitable for administration to a subject for treatment of a disease. The terms "patient," "subject," and "individual," are used interchangeably herein, to refer to mammals, including, but not limited to, humans, murines, simians, felines, canines, equines, bovines, porcines, ovines, caprines, mammalian farm and agricultural animals, mammalian sport animals, and mammalian pets. In certain embodiments of the invention, the subject is a companion animal, such as a dog, cat or horse.

The heterochimeric antibody engineered thereof is the result of the fusion of portion of the variable domain nucleotide sequences to constant region nucleotide sequences and the co-expression of these sequences to produce heterochimeric recombinant antibodies. Furthermore, the invention relates to the use of such heterochimeric antibodies antibodies and/or fragments thereof as immunotherapeutic agents for the treatment of disease in animals and as diagnostic agents.

Antibodies created according to the present invention offer several advantages, such as (i) reduced immunogenicity response upon repeated administration; (ii) increased potency mediated by an efficient recruitment of immune system responsible for effector functions in the targeted species; and (iii) increased half-life.

The present invention includes generation of heterochimeric antibodies and/or fragments thereof with the desired properties and their use in production. The heterochimeric antibodies from the present invention include a fragment of the variable region of an antibody derived from a species that is different than the one of the constant region. Thus, the heterochimeric antibodies and/or fragments thereof retain the specificities and high affinities with the desired effector functions in the target species.

The heterochimeric antibody of the present invention in particular embodiments may recognize any therapeutic target suitable for antibody therapy, for example a tumor-related antigen, an allergy- or inflammation-related antigen, a cardiovascular disease-related antigen, an autoimmune disease-related antigen or a viral or bacterial infection-related antigen.

"Native antibodies" are usually glycoproteins of about 150,000 daltons, composed of two identical light chains and two identical heavy chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (variable region) ($V_H$) followed by a number of constant domains (constant regions). Each light chain has a variable domain at one end ($V_L$) and a constant domain at its other end; the constant domain of the light chain is aligned with the first constant domain of the heavy chain, and the light-chain variable domain is aligned with the variable domain of the heavy chain.

The "light chains" of antibodies from any vertebrate species can be assigned to one of two clearly distinct types, called kappa and lambda.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains corresponding to the different classes of immunoglobulins are called alpha, delta, epsilon, gamma, and mu, respectively.

The term "variable domain" refers to the fact that certain portions of the variable domains differ in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4). The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" or "CDR" in the light chain variable domain and in the heavy chain variable domain as defined by Kabat et al., 5th Ed. Public Health Service, National Institutes of Health, Bethesda, Md. (1991) and/or as defined by (Chothia and Lesk, *Mol. Biol.* 196:901-917 (1987) and/or as defined as "AbM loops" by Martin, et al., *Proc. Natl. Acad. Sci. USA,* 86:9268-9272 (1989) and/or as defined by Lefranc et al., *Nucleic Acids Res,* 27:209-212 (1999) in the international ImMunoGeneTics information systems database. "Framework" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to readily crystallize. Pepsin treatment yields a binding cross-linking antigen.

"Fv" as used herein, refers to the minimum antibody fragment that contains a complete antigen-recognition and binding site. This region consists of a dimer of one heavy chain and one light chain variable domain.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "antibody" herein is used in the broadest sense and specifically covers monoclonal antibodies (including full length monoclonal antibodies), polyclonal antibodies, multispecific antibodies (e.g., bispecific antibodies), and antibody fragments exhibiting the desired biological activity. The desired biological activity will include at least binding to a cognate antigen and may further include complement activation and/or other effector functions.

"Antibody fragments" or "antigen-binding moiety" comprise a portion of a full length antibody, generally the antigen binding or variable domain thereof. Examples of antibody fragments include Fab, Fab', F(ab)$_2$, and Fv fragments; diabodies; linear antibodies; single-chain antibody molecules; and multispecific antibodies formed from antibody fragments that bind 2 or more different antigens.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific. For example, the monoclonal antibodies to be used in accordance with the present invention may be made by the hybridoma method first described by Kohler et al., Nature 256:495 (1975), or may be made by recombinant DNA methods. The monoclonal antibodies may also be isolated e.g. from phage antibody libraries.

Monoclonal antibodies are most frequently generated in mice by administration of the "antigen" and subsequent isolation of B-cells that make antibodies. The B-cells are then immortalized by fusion to another, stable cell type of the same species of the B cell to create a "hybridoma". An individual B-cell makes one specific antibody (i.e. is clonally monospecific), which is defined by its primary amino acid sequence and its underlying gene sequence. As used herein, the terms "heterohybridoma" and "heteromyeloma" refer to lymphocyte cell lines immortalized by fusion of lymphocytes and myelomas from two different species.

Monoclonal antibodies can be initially generated, for example, by immunizing animals with an antigen or with cells that express the antigen. The generation of a hybridoma starts with the immunization of mice or companion animals such as dogs. Immunization can be performed with several types of cells in the presence or absence of adjuvants. Cells can also be used to identify the hybridoma cell lines with the desired properties by ELISA, Biacore, FACS or other methodologies available to those in the art.

Cells suitable for use in the methods of monoclonal antibody preparation according to the present invention include: (1) Peripheral Blood Mononuclear Cells (PBMC) or fractions of PBMC enriched in certain type of cells collected from healthy or diseased companion animals such as dogs, cats, or horses. Lymphocytes are pre-incubated in some instances with factors including factors including growth factors such as EPO, SCF, TNFα, TGFβ, GMCSF, TPO, IL-1, IL-2, IL-3, IL-4, GCSF to increase the expression of the antigen prior to immunization. (2) Lymphoma cell lines or tumor cell lines established from healthy or diseased subjects optionally pre-incubated with factors listed above to increase the expression of the antigen prior to immunization. (3) Cell lines derived from tissues of healthy or diseased subjects pre-incubated in some instances with factors listed above to increase the expression of the antigen prior to immunization. (4) Cultured cells engineered to express an antigen coding region or fragment thereof, such as baculovirus-infected cells, bacterial cells, yeast cells, mammalian cells, plant cells, fungal cells and the like. The antigen in the form of DNA, RNA, protein, or peptide, can be included in any one of the fractions of the cell. (5) Magnetic Proteoliposome Particles (MPLs), which are prepared from cells expressing the antigen, such that the native conformation of the transmenbrane receptor is maintained, have been described previously (see e.g., Mirzabekov et al. *Nat. Biotechnol.* 18:649-654 (2000); Babcock et al. *J. Biol. Chem.* 276:38433-38440 (2001); PCT Publication WO 01/49265; U.S. Patent Application No. 20010034432).

In certain embodiments of the invention, the generation of monoclonal antibodies can be achieved using immunogens derived from DNA, peptides, or proteins. Hybridomas are generated by immunizing an animal, which can be for example, a mouse or a companion animal, or any animal that will give a suitable antibody response. In one aspect, immunization is performed by introducing into the animal an antigen-encoding nucleic acid, or a protein antigen, such as canine CD20 or CD52 or an immunogenic fragment thereof, or a nucleic acid encoding CD20 or CD52 or an immunogenic fragment thereof. The skilled artisan will appreciate that certain epitopes will be more immunogenic in an animal when removed from their native environment. Thus, a peptide corresponding to an epitope of an antigen conjugated to a carrier such as keyhole limpet hemocyanin, may elicit a stronger antibody response than either the peptide alone or the epitope when part of the native protein on which it is found. Such variations and other immunization schemes are known to the skilled artisan are included in the immunization methods of the invention.

The immunogen can be a plasmid carrying a nucleic acid sequence encoding an antigen or a fragment thereof. In other embodiments of the invention, monoclonal antibodies of the invention can be obtained by screening a library of antibody molecules or fragments thereof derived from immunization of animals. Monoclonal antibodies of the invention can also be obtained from libraries of antibodies or antibody-encoding nucleic acids.

As used herein the term "antigen" is understood to be any substance capable of stimulating antibody production. Also, the term "immunogen" is understood to include any substance used to induce an immune response.

The monoclonal antibodies herein may in some embodiments include "chimeric" antibodies in which a portion of the heavy and/or light chain is identical to or homologous with corresponding sequences from antibodies derived from a particular species or belonging to a particular antibody class or subclass, while the remainder of the chain(s) is identical to or homologous with corresponding sequences in antibodies from another species or belonging to another antibody class or subclass, as well as fragments of such antibodies, exhibiting the desired biological activity (See e.g., U.S. Pat. No. 4,816,567; and Morrison et al., *Proc. Natl. Acad. Sci. USA* 81:6851-6855 (1984)).

"Single-chainFv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun in The Pharmacology of Monoclonal Antibodies, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is short to allow pairing between the two domains on the same chain, the domains are forced to pair with the complementary domains of another chain and create two antigen-binding sites.

In certain aspects the present invention provides methods for adapting antibodies to the species of an intended therapeutic target. Generally, these methods include "mammalization" which is defined as a method for transferring donor antigen-binding information to a less immunogenic mammal antibody acceptor to generate useful therapeutic treatments. More specifically, the invention provides methods for felinization, equinization and caninization of antibodies.

"Caninization" is defined as a method for transferring non-canine antigen-binding information from a donor antibody to a less immunogenic canine antibody acceptor to generate treatments useful as therapeutics in dogs.

"Felinization" is defined as a method for transferring non-feline antigen-binding information from a donor antibody to a less immunogenic feline antibody acceptor to generate treatments useful as therapeutics in cats.

"Equinization" is defined as a method for transferring non-equine antigen-binding information from a donor antibody to a less immunogenic equine antibody acceptor to generate treatments useful as therapeutics in horses.

Caninized forms of non-canine antibodies provided herein are chimeric antibodies that contain minimal sequence derived from non-canine antibody. For the most part, caninized antibodies are canine antibody sequences ("acceptor" or "recipient" antibody) in which hypervariable region residues of the recipient are replaced by hypervariable region residues from a non-canine species ("donor" antibody) such as mouse, rat, rabbit, cat, dogs, goat, chicken, bovine, horse, llama, camel, dromedaries, sharks, non-human primates, human, humanized, recombinant sequence, or an engineered sequence having the desired properties. In some instances, framework region (FR) residues of the canine antibody are replaced by corresponding non-canine FR residues. Furthermore, caninized antibodies may include residues that are not found in the recipient antibody or in the donor antibody. These modifications are made to further refine antibody performance. The caninized antibody may also comprise at least a portion of an immunoglobulin constant region (Fc) of a canine antibody.

As used herein, "identity" refers to the sequence matching between two polypeptides, molecules or between two nucleic acids. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are identical at that position. The "percentage identity" between two sequences is a function of the number of matching positions shared by the two sequences divided by the number of positions compared.times.100. Such alignment can be provided using, for instance, the program Basic Local Alignment Search Tool (BLAST) from the National Center for Biotechnology Information NCBI.

In one preferred embodiment, the recombinant polypeptides, or fragments, derivatives, or modifications thereof, are specifically administered into a patient. In another embodiment, the recombinant polypeptide of the invention, or fragments, derivatives, or modifications thereof, are introduced into cells and/or a tissue while under in vitro or ex vivo conditions, prior to the transplantation of the cells and/or a tissue into a mammalian organism for the purpose of treating, preventing, reducing or otherwise lowering disease conditions or symptoms associated or mediated by the disease.

The terms "fragment" and "region" refer to portions of a polypeptide or nucleic acid molecule that contains at least 10%, 20%, 30%, 40%, 50%, 60%, 70%, 80%, 90%, 95%, or more of the entire length of the reference nucleic acid molecule or polypeptide.

The terms "polynucleotide," "nucleic acid," and "nucleic acid molecule," are used interchangeably herein to refer to polymeric forms of nucleotides of any length. The polynucleotides can contain deoxyribonucleotides, ribonucleotides, and/or their analogs. Polynucleotides can have any three-dimensional structure, and can perform any function, known or unknown. The term polynucleotide includes single-stranded, double-stranded, and triple helical molecules, and encompasses nucleic acids containing nucleotide analogs or modified backbone residues or linkages, which can be synthetic, naturally occurring, or non-naturally occurring, and which have similar binding properties as the reference nucleic acid.

"Oligonucleotide" refers generally to polynucleotides that are between 5 and about 100 nucleotides of single- or double-stranded DNA. For the purposes of this disclosure, the lower limit of the size of an oligonucleotide is two, and there is no upper limit to the length of an oligonucleotide. Oligonucleotides are also known as "oligomers" or "oligos" and can be prepared by any method known in the art including isolation from naturally-occurring polynucleotides, enzymatic synthesis and chemical synthesis.

The terms "polypeptide," "peptide" and "protein" are used interchangeably herein to refer to a polymer of amino acid residues of any length. Polypeptides can have any three-dimensional structure, and can perform any function, known or unknown. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ carboxyglutamate, and O-phosphoserine. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "conservatively modified variants" or "conservative variants" applies to both amino acid and nucleic acid sequences. With respect to particular nucleic acid sequences, conservatively modified variants refers to those nucleic acids which encode identical or substantially identical amino acid sequences; or for nucleic acids that do not encode an amino acid sequence, to nucleic acids that are substantially identical. As used herein, "substantially identical" means that two amino acid or polynucleotide sequences differ at no more than 10% of the amino acid or nucleotide positions, typically at no more than 5%, often at more than 2%, and most frequently at no more than 1% of the of the amino acid or nucleotide positions.

Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the alternate alanine codons without altering the encoded polypeptide. Such nucleic acid variations are "silent variations," which are one type of conservatively modified variants. Nucleic acid sequences encoding polypeptides described herein also encompass every possible silent variation of the nucleic acid. The skilled artisan will recognize that each amino acid codon in a nucleic acid (except AUG, which is ordinarily the only codon for methionine, and TGG, which is ordinarily the only codon for tryptophan) can be varied at one or more positions to code for the same amino acid. Accordingly, each silent variation of a nucleic acid that encodes a polypeptide is implicit in each described sequence with respect to the expression product.

"Complementarity" as applied to nucleic acids, refers to the ability of the nucleic acid to form hydrogen bond(s) with another polynucleotide sequence by either traditional Watson-Crick or other non-traditional types of base pairing. In reference to the nucleic molecules of the present invention, the binding free energy for a nucleic acid molecule with its target or complementary sequence is sufficient to allow the relevant function of the nucleic acid to proceed, e.g., enzymatic nucleic acid cleavage, RNA interference, antisense or triple helix inhibition. Determination of binding free energies for nucleic acid molecules is well known in the art. "Percent complementarity" refers to the percentage of contiguous residues in a nucleic acid molecule that can form hydrogen bonds (e.g., Watson-Crick base pairing) with another nucleic acid molecule. "Perfectly complementary" or "100% complementarity" means that all the contiguous nucleotides of a nucleic acid molecule will hydrogen bond with the same number of contiguous residues in a second nucleic acid molecule. "Substantial complementarity" and "substantially complementary" as used herein indicate that two nucleic acids are at least 90% complementary, typically at least 95% complementary, often at least 98% complementary, and most frequently at least 99% complementary over a region of more than about 15 nucleotides and more often more than about 19 nucleotides.

"Homology" is an indication that two nucleotide sequences represent the same gene or a gene product thereof, and typically means that that the nucleotide sequence of two or more nucleic acid molecules are partially, substantially or completely identical. When from the same organism, homologous polynucleotides are representative of the same gene having the same chromosomal location, even though there may be individual differences between the polynucleotide sequences (such as polymorphic variants, alleles and the like). In certain embodiments, a homolog can be found in a non-native position in the genome, e.g. as the result of translocation . . . .

The term "heterologous" refers to any two or more nucleic acid or polypeptide sequences that are not normally found in the same relationship to each other in nature. For instance, a heterologous nucleic acid is typically recombinantly produced, having two or more sequences, e.g., from unrelated genes arranged to make a new functional nucleic acid, e.g., a promoter from one source and a coding region from another source. Similarly, a heterologous polypeptide will often refer to two or more subsequences that are not found in the same relationship to each other in nature (e.g., a fusion protein).

The term "homolog" refers to a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 55%, 57%, 60%, 65%, 68%, 70%, more preferably 80% or 85%, and most preferably 90%, 95%, 98%, or 99% identical at the amino acid level or nucleic acid to a reference sequence.

"Similar" sequences are those which, when aligned, share identical and similar amino acid residues, where similar residues are conservative substitutions for corresponding amino acid residues in an aligned reference sequence. In this regard, conservative residues in a sequence is a residue that is physically or functionally similar to the corresponding reference residue, e.g., that has a similar size, shape, electric charge, chemical properties, including the ability to form covalent or hydrogen bonds, or the like. The "percentage similarity" between two sequences is a function of the number of positions that contain matching residues or conservative residues shared by the two sequences divided by the number of positions compared.times.100.

"Amino acid consensus sequence" as used herein refers to a hypothetical amino acid sequence that can be generated using a matrix of at least two, and preferably more, aligned amino acid sequences, and allowing for gaps in the alignment, such that it is possible to determine the most frequent amino acid residue at each position. The consensus sequence is that sequence which comprises the amino acids which are most frequently represented at each position. In the event that two or more amino acids are equally represented at a single position, the consensus sequence includes both or all of those amino acids. In some cases, amino acid consensus sequences correspond to a sequence or sub-sequence found in nature. In other cases, amino acid consensus sequences are not found in nature, but represent only theoretical sequences.

The amino acid sequence of a protein can be analyzed at various levels. For example, conservation or variability can be exhibited at the single residue level, multiple residue level, multiple residues with gaps etc. Residues can exhibit conservation of the identical residue or can be conserved at the class level. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). Other classes are known to one of skill in the art and may be defined using structural determinations or other data to assess substitutability.

Regarding amino acid sequences, one of skill in the art will recognize that individual substitutions, deletions or insertions to a nucleic acid, peptide, polypeptide, or protein sequence which alters, inserts or deletes a single amino acid or a small percentage of amino acids in the encoded sequence is a "conservatively modified variant" where the alteration results in the substitution of an amino acid with a chemically similar amino acid. Conservative substitution tables detailing functionally similar amino acids are well known in the art. Such conservatively modified variants are in addition to and do not exclude functionally equivalent polymorphic variants, homologs, and alleles of the invention.

As used herein, when one amino acid sequence (e.g., a first VH or VL sequence) is aligned with one or more additional amino acid sequences (e.g., one or more VH or VL sequences in a database), an amino acid position in one sequence (e.g., the first VH or VL sequence) can be compared to a "corresponding position" in the one or more additional amino acid sequences. As used herein, the "corresponding position" represents the equivalent position in the sequence(s) being compared when the sequences are optimally aligned, i.e., when the sequences are aligned to achieve the highest percent identity or percent similarity.

As used herein, the term "antibody database" refers to a collection of two or more antibody amino acid sequences (a "plurality" or "multiplicity" of sequences), and typically refers to a collection of tens, hundreds or even thousands of antibody amino acid sequences. An antibody database can store amino acid sequences of, for example, a collection of antibody VH regions, antibody VL regions or both, or can store a collection of framework sequences. In one embodiment, the antibody database is a database comprising or consisting of germline antibody sequences. In another embodiment, the antibody database is a database comprising or consisting of mature antibody sequences (e.g., a Kabat database of mature antibody sequences). In another embodiment, the antibody database comprises or consists of sequences selected for one or more properties. In another embodiment, the antibody database comprises or consists of consensus sequences. In another embodiment, the antibody database comprises or consists of similar sequences. In yet another embodiment, the antibody database comprises or consists of sequences from major antibody clans (Das et al., *Immunogenetics*, 60:47-55 (2008); Das et al., *Proc. Nail. Ac. Sci. USA*. 105:16647-16652 (2008)).

As used herein, the term "property" is a property of a polypeptide which is desirable and/or advantageous to one of skill in the art, e.g., in order to improve the manufacturing properties or therapeutic efficacy of the polypeptide. In one embodiment, the functional property is improved stability. In another embodiment, the functional property is improved solubility. In yet another embodiment, the functional property is non-aggregation. In still another embodiment, the functional property is an improvement in expression. In certain embodiments, the functional property is an improvement in antigen binding affinity.

In the methods of the invention, the sequence of the antibody of interest can be compared to the sequences within one or more of a variety of different types of antibody sequence databases. For example, in one embodiment, the antibody VH, VL or VH and VL amino acid sequences of the database are germline antibody VH, VL or VH and VL amino acid sequences. In another embodiment, the antibody VH, VL or VH and VL amino acid sequences of the database are rearranged, affinity matured antibody VH, VL or VH and VL amino acid sequences. In yet another embodiment, the antibody VH, VL or VH and VL amino acid sequences of the database are pseudogene antibody VH, VL or VH and VL amino acid sequences.

In the methods of the invention, the sequence of the antibody to modify can be compared with all sequences within an antibody database or, alternatively, only a selected portion of the sequences in the database can be used for comparison purposes. That is, the database can be limited, or constrained, to only those sequences having a high percentage similarity or identity to the antibody of interest. Thus, in one embodiment of the method of the invention, the database is a constrained database in which only those antibody VH, VL or VH and VL amino acid sequences having high similarity to the VH, VL or VH and VL amino acid sequences are included in the database.

The methods of the invention can be combined with other methods known in the art for analyzing antibody structure and antibody structure/function relationships. For example, in a one embodiment, the methods of the invention are combined with molecular modeling to identify additional potentially problematic residues. Methods and software for computer modeling of antibody structures are established in the art and can be combined with the methods of the invention. The role of sequences can be further determined by examining, for example, local and non-local interactions, canonical residues, interfaces, exposure degree and .beta.-turn propensity. Molecular modeling methods known in the art can be applied, for example, to select "best fit" sequences if a panel of possible sequences is under consideration.

A sequence identified to be utilized for mammalization, caninization, felinization or equinization can be mutated using one of several possible mutagenesis methods well established in the art. For example, site directed mutagenesis can be used make a particular amino acid substitution at the amino acid position of interest. Site directed mutagenesis also can be used to create a set of mutated sequence sin which a limited repertoire of amino acid substitutions have been introduced at the amino acid position of interest.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived from.

Immunogenic, as used herein, refers to antigens, (including native antigens, fragments, mutant, and derivatives thereof, as well as recombinant and synthetic antigens), that, when introduced into an animal, elicit an immune response, such as a humoral or antibody response.

As used herein, the term "not immunogenic" or "non-immunogenic" means that an antigen, such as an antibody, or other molecule, does not raise an antibody response of sufficient magnitude to reduce the effectiveness of continued administration of the antibody in the majority of treated patients for sufficient time to achieve therapeutic efficacy.

As used herein, the term "therapeutic" encompasses the full spectrum of treatments for a disease or disorder. A "therapeutic" agent of the invention may act in a manner that is prophylactic or preventive, including those that incorporate procedures designed to target individuals that can be identified as being at risk (pharmacogenetics); or in a manner that is ameliorative or curative in nature; or may act to slow the rate or extent of the progression of a disease or disorder; or may act to minimize the time required, the occurrence or extent of any discomfort or pain, or physical limitations associated with recuperation from a disease, disorder or physical trauma; or may be used as an adjuvant to other therapies and treatments.

"Treatment," as used herein, covers any administration or application of remedies for disease in an animal, including a human, and includes inhibiting the disease, i.e., arresting its development; relieving the disease, i.e., causing its regression; and eliminating the disease, i.e., causing the removal of diseased cells or restoration of a non-diseased state. Treatment refers to both therapeutic treatment and prophylactic or preventative measures. Those in need of treatment include those already with the disorder as well as those in which the disorder is to be prevented.

A "pharmaceutical composition" or "pharmaceutically acceptable composition" of antibodies, polypeptides, or polynucleotides herein refers to a composition that usually contains a pharmaceutically acceptable carrier or excipient that is conventional in the art and which is suitable for administration into a subject for therapeutic, diagnostic, or prophylactic purposes. For example, compositions for oral administration can form solutions, suspensions, tablets, pills, capsules, sustained release formulations, oral rinses, or powders.

The term "combination therapy" refers to a therapeutic regimen that involves the provision of at least two distinct therapies to achieve an indicated therapeutic effect. For example, a combination therapy may involve the administration of two or more chemically distinct active ingredients, for example, a chemotherapeutic agent and an antibody. Alternatively, a combination therapy may involve the administration of an antibody and/or one or more chemotherapeutic agents, alone or together with the delivery of another treatment, such as radiation therapy and/or surgery. In the context of the administration of two or more chemically distinct active ingredients, it is understood that the active ingredients may be administered as part of the same composition or as different compositions. When administered as separate compositions, the compositions comprising the different active ingredients may be administered at the same or different times, by the same or different routes, using the same of different dosing regimens, all as the particular context requires and as determined by the attending veterinarian or attending caregiver.

The term "monotherapy" refers to a treatment regimen based on the delivery of one therapeutically effective compound, whether administered as a single dose or several doses over time.

"Immune conditions" are a generic name for a wide range of diseases including arthritis, psoriasis, inflammatory bowel disease, multiple sclerosis, myocardial infarction, stroke, hemolytic anemia, atopic dermatitis, skin disorders, and the like, in which the immune system or a part thereof, such as a cell of the immune system, is abnormal or causes a disease state. Immune conditions include primary defects in an immune cell, tissue or organ, as well as "autoimmune conditions," in which the normal mechanisms for preventing immune recognition of self antigens is defective, resulting in a disease or disorder involving a non-immune cell, tissue or organ type. Leukemias and lymphoma's are primary immune disorders, while multiple sclerosis and lupus are believed to be of autoimmune origin.

A multitude of therapeutic agents have been developed over the past few decades for the treatment of various types of immune conditions for humans and these have also been used for the treatment of immune conditions in companion animals. The most commonly used types of anti-immune agents include: immunosuppressant agents (e.g., cyclosporine, thiopurine, prednisone), and analgesic and antipyretic (e.g., aspirin, ibuprofen, naproxen, celecoxib, nimesulide, licofelone, omega-3-fatty acids), each of which may be administered simultaneously, sequentially or in a common dosage regimin with antibodies of the invention.

"Cancer" as used herein, refers to any abnormal cell or tissue growth, e.g., a tumor, which can be malignant or non-malignant. Cancer is characterized by uncontrolled proliferation of cells that may or may not invade the surrounding tissue and, hence, may or may not metastasize to new body sites. Cancer encompasses carcinomas, which are cancers of epithelial cells (e.g. squamous cell carcinoma, adenocarcinoma, melanomas, and hepatomas). Cancer also encompasses sarcomas, which are tumors of mesenchymal origin, (e.g. osteogenic sarcomas, leukemias, and lymphomas). Cancers can involve one or more neoplastic cell type. Cancer a generic name for a wide range of cellular malignancies characterized by unregulated growth, lack of differentiation, and the ability to invade local tissues and metastasize. These neoplastic malignancies affect, with various degrees of prevalence, every tissue and organ in the body. A multitude of therapeutic agents have been developed over the past few decades for the treatment of various types of cancer for humans and have been used off-label or reformulated for the treatment of cancer in companion animals. The most commonly used types of anti-cancer agents include: DNA-alkylating agents (e.g., cyclophosphamide, ifosfamide), anti-metabolites (e.g., methotrexate, a folate antagonist, and 5-fluorouracil, a pyrimidine antagonist), microtubule disrupters (e.g., vincristine, vinblastine, paclitaxel), DNA intercalators (e.g., doxorubicin, daunomycin, cisplatin), and immunosuppressant (e.g., prednisone), each of which may be administered simultaneously, sequentially or in a common dosage regimin with antibodies of the invention.

Antibodies (mAbs) that can be subjected to the techniques set forth herein include monoclonal and polyclonal mAbs, and antibody fragments such as Fab, Fab', F(ab')2, Fd, scFv, diabodies, antibody light chains, antibody heavy chains and/or antibody fragments derived from various sources. An antibody is obtained from a sequence donor species. More particularly, the nucleic acid or amino acid sequence of the variable portion of the light chain, heavy chain or both, of the donor species antibody has specificity for a desired antigen. The donor species is any species which was used to generate the antibodies or antibody libraries, e.g., mouse, rat, rabbit, cat, dogs, goat, chicken, bovine, horse, llama, camel, dromedaries, sharks, non-human primates, human, humanized, recombinant sequence, engineered sequence, etc. Techniques for generating and cloning monoclonal antibodies are well known to those skilled in the art.

After sequencing the antibody obtained from the donor species or from a library, the variable regions (VH and VL) are separated into discrete regions such as leader sequences, frameworks (FRs) and CDRs using any published definition of CDRs and frameworks (e.g., Kabat, Chothia, AbM, contact definition and any combination thereof; and any others known to those skilled in the art). In a particular embodiment, FRs and CDRs are identified with reference to the Kabat definitions.

In one aspect, after determining the variable domains with its individual framework region and CDRs from an originating species, i.e., FR1, FR2, FR3, FR4, CDR1, CDR2, and CDR3, a set of FR4 from the target species is selected to replace the FR4 from the donor species.

In another aspect, a set of FR1 from the target species is selected to replace the FR1 from the donor species.

In another aspect, one or more FR are from the target species.

In another aspect, both the FR1 and FR4 are from the target species.

Thus in one embodiment the antibody would have a constant region, and FR1 and/or FR4 derived from a target species, and FR2, FR3, CDR1, CDR2, and CDR3 derived from a donor species.

A "chimeric antibody" comprises a sequence of the constant region or fragment thereof from a target species and the variable domain containing the contiguous sequence FR1-CDR1-FR2-CDR2-FR3-CDR3-FR4 from the donor species fused to the constant domain of the target species. FR4 regions are derived from the J gene fragments for the light chains and for heavy chains and can be viewed as an extension of the constant domains.

Whenever it appears herein, a numerical range such as "1 to 100" refers to each integer in the given range; e.g., "1 to 100 nucleotides" means that the nucleic acid can contain only 1 nucleotide, 2 nucleotides, 3 nucleotides, etc., up to and including 100 nucleotides.

At that point, with respect to the constant domains of light chains, a constant domain or fragment thereof from the target species belonging to the kappa light chain type, or the constant domain or fragment thereof from the target species belonging to the lambda light chain type may be fused to the light chain heterochimeric variable domains. It is contemplated that a heterochimeric antibodies and/or fragments thereof could comprise a FR from a lambda variable domain fused together with a constant domain of a kappa light chain type or a FR sequence from a kappa variable domain fused together with a constant domain of a lambda chain. It is also contemplated that any combination of FR from the target species can be made with any type of light chains of the originating species.

With respect to the constant domains of heavy chains, a constant domain or fragment thereof of any subclass from the target species may be fused to the heavy chain heterochimeric variable domains.

With respect to the pairing of the heterochimeric heavy chain and the heterochimeric light chain, any combination can be made.

The recombinant antibody of the method disclosed herewith can be an IgG, IgM, IgD, IgE, IgH, or IgA antibody. In some embodiments, the antibody is an IgG antibody. More particularly, the antibody can be an $IgG_1$, $IgG_2$, $IgG_3$, or $IgG_4$ antibody. The donor species antibody sequence can be, for example from a mouse, rat, rabbit, cat, dogs, goat, chicken, bovine, horse, llama, camel, dromedaries, sharks, non-human primates, human, humanized, recombinant sequence, consensus sequences, pseudogene sequences, or an engineered sequence. The target or acceptor species antibody sequence can be, for example, from a canine antibody, a feline antibody, an equine antibody or a human antibody.

The engineering of the recombinant antibody of the claimed invention comprise can be created by introducing modifications, additions or deletions to a nucleic acid encoding the antibody can be introduced by a method comprising recombination, error-prone PCR, shuffling, oligonucleotide-directed mutagenesis, assembly PCR, sexual PCR mutagenesis, in vivo mutagenesis, site-specific mutagenesis, gene reassembly, synthetic ligation reassembly or a combination thereof.

Further envisioned within the scope of this invention is the usage of the recombinant nucleic acids or proteins, or fragments or derivatives thereof, for the treatment of all companion animal diseases and/or conditions that are mediated or associated with the onset of inflammation, as well as companion animal diseases and/or conditions that are mediated or associated with autoimmunity. Such diseases and/or conditions are referred to herein as inflammatory disorders and include but are not restricted to inflammation, autoimmune disease and immune-mediated.

In a further aspect, the invention features pharmaceutical compositions in which antibodies of the present invention are provided for therapeutic or prophylactic uses. The invention features a method for treating a dog subject having a particular antigen, e.g., one associated with disease. The method includes administering a therapeutically effective amount of a recombinant antibody specific for the particular antigen, with the recombinant antibody described herein.

The amount of antibody useful to produce a therapeutic effect can be determined by standard techniques well known to those of ordinary skill in the art. The antibodies will generally be provided by standard technique within a pharmaceutically acceptable buffer, and may be administered by any desired route. The route of administration of the antibody or antigen-binding moiety of the invention may be oral, parenteral, by inhalation or topical. The term parenteral as used herein includes intravenous, intramuscular, subcutaneous, rectal, vaginal or intraperitoneal administration.

Antibodies produced in the manner described above, or by equivalent techniques, can be purified by a combination of affinity and size exclusion chromatography for characterization in functional biological assays. These assays include determination of specificity and binding affinity as well as effector function associated with the expressed isotype, e.g., ADCC, apoptosis, or complement fixation. Such antibodies may be used as passive or active therapeutic agents against a number of diseases, including B cell lymphoma, T cell lymphoma, autoimmune diseases, inflammatory diseases, infectious diseases, and transplantation.

In preferred embodiments of the above aspects, the antigen is a tumor antigen, an antigen involved in an immune disorder, an antigen involved in an autoimmune response, a receptor expressed on a host cell or available in blood circulation or secreted by a cell and the recombinant antibody is able to either deplete undesired cells or to block or stimulates receptor functions, or neutralizes active soluble products.

The antibodies (or fragments thereof) of this invention may also be useful for treating tumors in companion animals. More specifically, they should be useful for reducing tumor size, inhibiting tumor growth and/or prolonging the survival time of tumor-bearing animals. Accordingly, this invention also relates to a method of treating tumors in a dog or other animals by administering an effective dose. An effective dose is expected to be in the range of about 0.05 to 100 milligrams per kilogram body weight per day.

In a particular embodiment, the invention provides antibodies to CD20. The canine CD20 is a non-glycosylated integral membrane phosphoprotein expressed on the surface of almost all normal and malignant B cells. It has four membrane spanning hydrophobic regions and a short extracellular loop between the third and fourth transmembrane domain.

The CD20 protein is predicted to contain domains of amino acid sequences consisting of two extracellular domains, four transmembrane domains, and three intracellular domains as human CD20.

The amino acid sequence of canine CD20 shows sequence similarities with those of human and mice. The amino acid sequences of canine CD20 exhibit a high degree of similarity with the human gene, suggesting a similar biological function. Despite the sequence homology between the canine and human CD20 sequence, Rituximab, a monoclonal antibody to the human CD20 antigen does not react with canine B cells probably due to the lack of homology between humans and dogs in the epitope of the extracellular domain of CD20 recognized by Rituximab (Veterinary Journal, 2006, vol 171, 556). There are several reported versions of canine CD20. In one embodiment, the canine CD20 is of SEQ ID NO: 67:

```
MTTPRNSMSGTLPVDPMKSPTAMYPVQKIIPKRMPSVVGPTQNFFMRESK

TLGAVQIMNGLFHIALGSLLMIHTDVYAPICITMWYPLWGGIMFIISGSL

LAAADKNPRKSLVKGKMIMNSLSLFAAISGIIFLIMDIFNITISHFFKME

NLNLIKAPMPYVDIHNCDPANPSEKNSLSIQYCGSIRSVFLGVFAVMVIF

TFFQKLVTAGIVENEWKKLCSKPKSDVVVLLAAEEKKEQPIETTEEMVEL

TEIASQPKKEEDIEIIPVQEEEEELEINFAEPPQEQESSPIENDSIP
```

Canine antibody against the CD20 antigen expressed by normal and malignant B lymphocytes. The antibody is produced in mammalian cells (CHO or Per.C6) and meets manufacturing and purification specifications. The product is a sterile, clear, colorless, preservative free liquid concentrate for parenteral administration.

In another embodiment, the invention provides antibodies to CD52. The small cell-surface glycoprotein CD52, commonly called the CAMPATH-1 antigen, is a widely distributed membrane-bound protein occurring on a variety of cells including but not limited to lymphocytes, monocytes, thymocytes, epithelial cells, macrophages, peripheral blood cells, dendritic cells, eosinophils, mast cells and several tumor cell lines such as osteogenic tumor cells. In some cases, CD52 or a fragment thereof may be a soluble protein.

A variety of cells expressing the antigen CD52 are associated with diseases such as cancers and immune conditions. Several studies have demonstrated or disclosed that neutralization of human CD52-expressing cells can improve tumor cell or neoplasia either alone or in combination with other anti-cancer or chemotherapeutic agents or treatments.

Myeloid lineage immune cell, containing a number of membrane-bound proteins including CD52, secrete a variety of cytokines and enzymes that result in inflammation. As some of these substances occur in secretory vesicles that appear granular, the process of secretion is sometimes called degranulation. Rapid degranulation by mast cells contributes to the pathology of asthma, anaphylaxis, and other allergic responses, while slower degranulation by mast cells contributes to arthritis and other types of chronic inflammation. The release of inflammatory cytokines and enzymes by mast cells can result in tissue damage, further attraction of mast cells, resulting in further tissue damage . . . .

Macrophages are white blood cells found within tissues produced by the division of monocytes that contain a number of membrane-bound proteins including CD52. These cells are involved in the innate immunity and cell-mediated immunity with a role of phagocytosis of cellular debris and pathogens and to stimulate lymphocytes and other immune cells. Macrophages are involved in many diseases of the immune system. Macrophages are the predominant cells involved in creating the progressive plaque lesions of atherosclerosis. Macrophages are believed to promote proliferation and inflammation of cancerous cells. The arsenal of veterinary medicine is limited when it comes to addressing immune conditions and cancer. Most veterinary therapeutic agents have been borrowed from human therapeutics, often with imperfect results. There is a thus a need for improved and more specific treatments and biologic agents for use in animals, such as companion animals. Novel and specific treatments targeting proteins on the surface of cells involved in animal diseases may be used to diagnose and treat such diseases with polyclonal antibodies or fragment thereof, monoclonal antibodies or fragment thereof, polypeptides or fragment thereof and other agents which specifically recognize the cell surface targets. In particular, novel antibodies and other agents disclosed herein which specifically recognize targets on the surface of cells that can modulate, (reduce and/or enhance), the disease-promoting activities of cells carrying antigens such as CD20 and/or CD52. The present invention provides antibodies and polypeptides targeting antigens that are capable of inhibiting the disease-associated activities of cells expressing these antigens either on the membrane or released in blood circulation. In another aspect, the invention provides novel compounds for use in diagnostic assays, and for use as antigens or for selecting antibodies to antigens such as CD20 and CD52.

The invention thus provides: heterochimeric antibodies and/or fragments thereof that include (i) hypervariable region sequences wholly or substantially identical to sequences found in antibodies from a donor species; (ii) constant region sequences wholly or substantially identical to sequences found in antibodies from a target species which is different from the donor species; and (iii) heavy and/or light chain variable framework sequences which contain at least three contiguous non-CDR residues corresponding to sequences found in antibodies from a target species and at least three contiguous non-CDR residues corresponding to sequences found in antibodies from a donor species.

In certain aspects, the antibody of the invention includes within the variable framework sequences, at least four, five, six or more contiguous non-CDR residues corresponding to sequences found in antibodies from a target species.

In certain aspects, the light chain variable region sequence of the antibody of the invention includes at least four, five, six or more contiguous non-CDR residues corresponding to sequences found in antibodies from a donor species.

The donor species can be any species in which antibodies can be generated, such as a rodent (e.g. mouse, rat, hamster and the like).

The target species can be any mammal, including humans, for which treatment is desired, e.g., in which it is desirable to reduce the presence of neutralizing anti-antibody antibodies in an antibody therapy. In certain embodiments, the target species is a companion animal selected from a dog, cat, and horse. Companion animals are generally animals that are kept as pets.

Antibodies of the invention include a framework region (FR) (e.g. a lambda or kappa variable domain) of a donor species antibody fused to a constant domain (kappa or lambda light chain) from a target species antibody. In particular, the antibodies of the invention include donor light chains that contain FR4 and/or FR1 from a target species animal.

In certain embodiments, the antibodies of the invention include heavy chain variable regions from a target species antibody. In particular aspects of the invention, the heavy chain variable region the FR1 is a target species sequence.

The antibody will be directed to and bind an antigen of the target species, such as a dog, cat or horse antigen. The antigen can be, for example, a tumor antigen, such as a canine, feline or equine tumor antigen. In some aspects, antibody will also bind to homologous antigens from other mammals, such as human antigens including human tumor antigen. In other embodiments of the invention, the antigen is associated with a cardiovascular disease, an autoimmune disease, an inflammatory disease or a viral or bacterial infection related disease. Antigens contemplated as targets for the antibodies of the present invention include, but are not limited to antigens that are known in the art, such as: CD2, CD3, CD4, CD5, CD8, CD11a, CD11b, CD18, CD19, CD20, CD22, CD23, CD25, CD26, CD28, CD29, CD11, CD33, CD34, CD38, CD40, CD40L, CD41, CD44, CD45, CD52, CD54 (ICAM-1), CD61, CD71, CD74, CD79, CD80, CD87, CD104, CD120, CD121, CD122, CD123, CD126, CD128, CD133, CD135, CD150, CLL-1, CD117 (c-Kit), CD152, CD153, Flk-2/Flt3, Gr-1 Ly-6, Sca-1, IGF1R, HER2/neu, EpCam, RANK-L, TRAIL-1, HGF (hepatocyte growth factor), TNF.alpha., TNF.beta., IL-1, IL-6, IL-8, IL-13, IL-17, C5a, TCR, adhesion molecules, the neu oncogene product, MDR-1 (P-glycoprotein), TGFA and its receptor, EGF, PDGF, VEGF, and their receptors, and the chemokines.

In certain embodiments antibodies of the present invention target antigens associate with a particular disease or disorder, such as acute inflammation, rheumatoid arthritis, transplant rejection, asthma, allergic inflammation, restenosis, arterial restenosis, inflammatory bowel disease, uveitis, multiple sclerosis, psoriasis, wound healing, lupus erythematosus, allergic rhinitis, atopic dermatitis, food allergies, diabetes mellitus, dermatitis, thrombotic thrombocytopenic purpura, encephalitis, leukocyte adhesion deficiency, rheumatic fever, psoriatic arthritis, osteoarthritis, ocular inflammatory disorders, progressive systemic sclerosis, primary biliary cirrhosis, CNS inflammatory disorder, antigen-antibody complex mediated diseases, autoimmune hemolytic anemia, ischemic heart disease, atherosclerosis, post-dialysis syndrome, leukemia, acquired immune deficiency syndrome, septic shock, lipid histiocytosis, and cancer.

Of particular interest are antigens CD20, CD52, HER2/neu, and IL-6, as well as the epitope recognized by mAb 231 (ATCC HB-9401). The skilled artisan will appreciate that the antigen is preferably isolated or derived from the target species (e.g. canine, feline or equine), but suitable cross-reactive antibodies can in some cases be generated by using an antigen from a xenogenic species.

1.1. The antibody of any of the previous embodiments wherein the complementarity determining regions and framework regions are defined in accordance with Kabat.

1.2. The antibody of any of the previous embodiments wherein the constant region of the antibody is modified to enhance a cytotoxic effector functions selected from ADCC, antibody dependent cellular phagocytosis (ADCP), and complement dependent cytotoxicity (CDC).

In a further embodiment, the invention provides

2. Antibody 2, which is an antibody to canine or feline or equine CD20, CD52, HER2/neu, IL-6, IL-6 receptor, or the epitope recognized by mAb 231 (ATCC HB-9401).

2.1. Antibody 2 wherein the antibody is to canine or feline or equine CD20.

2.2. Antibody 2.1 wherein the antibody is derived from or has substantially the same hypervariable domain as an antibody raised against an immunogenic construct comprising or expressing a peptide containing the sequence of one or more extracellular loops of CD20.

2.3. Any of Antibodies 2-2.2 wherein the antibody induces apoptosis of cells expressing CD20.

2.4. Any of Antibodies 2-2.3 wherein the antibody suppresses growth of cells expressing CD20.

2.5. Any of Antibodies 2-2.4 wherein the antibody causes the death of cells expressing CD20 by antibody dependent cell-mediated cytotoxicity (ADCC).
2.6. Any of Antibodies 2-2.5 wherein the antibody causes the death of cells expressing CD20 by complement-dependent cytotoxicity (CDC).
2.7. Any of Antibodies 2-2.6 wherein the antibody is to feline CD20, e.g., of SEQ ID NO.:69.
2.8. Any of Antibodies 2-2.6 wherein the antibody is to canine CD20, e.g. of SEQ ID NO.:67.
2.9. Antibody 2.8 wherein the antibody is derived from or has substantially the same hypervariable domain as an antibody raised against an immunogenic construct comprising or expressing a peptide containing a sequence selected from one or more of the following sequences: SEQ ID NO.:67 and SEQ ID NO.:69.
2.10. Antibody 2.8 or 2.9 wherein the antibody specifically recognizes an epitope on the extracellular loop of canine CD20, wherein the epitope comprises or is found within a region of the CD20 comprising or expressing a peptide containing a sequence selected from one or more of the sequences of residues 74-84, 178-188, 154-170, 140-146, 162-173, 148-159, 142-153, 148-169, 166-177, or 161-176 of SEQ ID NO:67.
2.11. Any of Antibodies 2-2.6 wherein the antibody is to equine CD20.
2.12. Antibody 2 wherein the antibody is to canine or feline or equine CD52.
2.13. Antibody 2.12 wherein the antibody is derived from or has substantially the same hypervariable domain as an antibody raised against an immunogenic construct comprising or expressing a peptide containing the sequence of one or more extracellular loops of CD52.
2.14. Any of Antibodies 2.12 or 2.13 wherein the antibody induces apoptosis of cells expressing CD52.
2.15. Any of Antibodies 2.12 or 2.13 wherein the antibody suppresses growth of cells expressing CD52.
2.16. Any of Antibodies 2.12 or 2.13 wherein the antibody causes the death of cells expressing CD52 by antibody dependent cell-mediated cytotoxicity (ADCC).
2.17. Any of Antibodies 2.12 or 2.13 wherein the antibody causes the death of cells expressing CD52 by complement-dependent cytotoxicity (CDC).
2.18. Any of Antibodies 2.16-2.6 wherein the antibody is to feline CD52.
2.19. Any of Antibodies 2-2.6 wherein the antibody is to canine CD52.
2.20. Antibody 2.19 wherein the antibody is derived from or has substantially the same hypervariable domain as an antibody raised against an immunogenic construct comprising or expressing a peptide containing a sequence selected from one or more of the sequences of residues 4-18, 20-26, 30-39, 36-47, and/or 49-64 of SEQ ID NO:72.
2.21. Antibody 2.8 or 2.9 wherein the antibody specifically recognizes an epitope on the extracellular loop of canine CD52, wherein the epitope comprises or is found within a region of the CD52 selected from residues 4-18, 20-26, 30-39, 36-47, and/or 49-64 of SEQ ID NO:72.
2.22. Any of Antibodies 2-2.6 wherein the antibody is to equine CD52.
2.23. Any of Antibodies 2-2.22 wherein the antibody comprises hypervariable sequences from a donor species antibody and constant region sequences from a target species.
2.24. Any of Antibodies 2.23 wherein the antibody is caninized.
2.25. Any of Antibodies 2.23 wherein the antibody is felinized.
2.26. Any of Antibodies 2.23 wherein the antibody is equinized.
2.27. Any of Antibodies 2.23 to 2.26 wherein the antibody is a heterochimeric antibody of any of Antibodies 1-1.35.
2.28. Any of Antibodies 2-2.22 wherein the antibody is monoclonal and is fully canine.
2.29. Any of Antibodies 2-2.22 wherein the antibody is monoclonal and is fully feline.
2.30. Any of Antibodies 2-2.22 wherein the antibody is monoclonal and is fully equine.

The invention further provides a. a method of treating a patient suffering from a disease or condition characterized by the presence of abnormal cells expressing a target antigen comprising administering a therapeutically effective amount of an antibody binding to such target antigen, wherein the antibody is selected from Antibody 1-1.35 or 2-2.30.
b. a method of treating a patient suffering from a disease or condition characterized by the presence of abnormal cells expressing CD20 comprising administering a therapeutically effective amount of an antibody selected from Antibody 2-2.11 and 2.23-2.30.
c. Method b) wherein the patient is a dog.
d. Method c) wherein the condition to be treated is canine lymphoma.
e. Method a) wherein the disease is selected from the group consisting of: acute inflammation, rheumatoid arthritis, transplant rejection, asthma, allergic inflammation, restenosis, arterial restenosis, inflammatory bowel disease, uveitis, multiple sclerosis, psoriasis, wound healing, lupus erythematosus, allergic rhinitis, atopic dermatitis, food allergies, diabetes mellitus, dermatitis, thrombotic thrombocytopenic purpura, encephalitis, leukocyte adhesion deficiency, rheumatic fever, psoriatic arthritis, osteoarthritis, ocular inflammatory disorders, progressive systemic sclerosis, primary biliary cirrhosis, CNS inflammatory disorder, antigen-antibody complex mediated diseases, autoimmune hemolytic anemia, ischemic heart disease, atherosclerosis, post-dialysis syndrome, leukemia, acquired immune deficiency syndrome, septic shock, lipid histiocytosis, and cancer.
f. Method a, b, c or d or e further comprising administration of chemotherapy.
g. Method f wherein the chemotherapy comprises administration of one or more agents selected from cyclophosphamide, doxorubicin, vincristine, prednisone, L-asparaginase, cytoxan and adriamycin.
h. Method for g wherein the chemotherapy spares or enhances effector cells, e.g., so as to enhance or reduce interference with ADCC effects of antibody on cancer cells.
i. Any of the foregoing methods further comprising administration of a corticosteroid, e.g., prednisone.
j. Any of the foregoing methods further comprising administration of radiation.
k. A method of treating a patient suffering from a disease or condition characterized by the presence of abnormal cells expressing CD52 comprising administering a therapeutically effective amount of an antibody selected from Antibody 2.12-2.30.
l. Method k) wherein the patient is a dog.
m. Method l) wherein the condition to be treated is canine lymphoma.

n. Any of the foregoing methods comprising co-administration of antibody to CD20 and CD52.

o. Any of the foregoing methods wherein the antibody is administered in a method to treat or inhibit recurrence of cancer following treatment with radiation or chemotherapy.

The invention further provides pharmaceutical compositions comprising any of antibodies 1-1.35 or 2-2.30, e.g., for use in any of methods a-o.

The invention further provides the use of any of antibodies 1-1.35 or 2-2.30 as pharmaceuticals, or in the manufacture of a medicament for use in any of the methods a-o.

The invention further provides a cell line stably expressing any of antibodies 1-1.35 or 2-2.30, for example a CHO cell line stably expressing any of antibodies 1-1.35 or 2-2.30.

The invention further provides a vector or vectors expressing at least one heavy chain and at least one light chain of any of antibodies 1-1.35 or 2-2.30.

The invention further provides a method of making an antibody comprising transforming a cell line with a vector or vectors expressing at least one heavy chain and at least one light chain of any of antibodies 1-1.35 or 2-2.30.

In another embodiment the invention provides a method of diagnosing a disease or condition treatable with the antibodies of the invention, comprising obtaining a tissue sample and measuring binding by one of the antibodies of the invention, together with diagnostic kits for performing such a method comprising an antibody of the invention, e.g., any of antibodies 1-1.35 or 2-2.30.

Other features and advantages of the invention are apparent from the following description of the preferred embodiments thereof, and from the claims.

EXAMPLE 1

Heterochimeric Antibodies

The following EXAMPLE provides general representations of heterochimeric antibodies, which are constructed according to standard techniques using the sequences and general patterns illustrated below. In the examples listed below, the CDRs are defined using the Kabat nomenclature. Databases containing these sequences are built from various sources such as NCBI and others (Das et al., *Immunogenetics*, 60:47-55 (2008); Das et al., *Proc. Natl. Ac. Sci. USA*. 105:16647-16652 (2008)).

I. Antibody Variable Domains

Illustrated below in Table 1, are diagrammatic representations of the heterochimerization for the light chain antibodies, showing contiguous sequences of discrete immunoglobulin domains.

TABLE 1

| | |
|---|---|
| AVD 1: | FR1-CDR1-FR2-CDR2-FR3-CDR3-FR4$_{T\text{-}Lambda}$-C$_{T\text{-}Lambda}$ |
| AVD 2: | FR1-CDR1-FR2-CDR2-FR3-CDR3-FR4$_{T\text{-}Kappa}$-C$_{T\text{-}Lambda}$ |
| AVD 3: | FR1-CDR1-FR2-CDR2-FR3-CDR3-FR4$_{T\text{-}Lambda}$-C$_{T\text{-}Kappa}$ |
| AVD 4: | FR1-CDR1-FR2-CDR2-FR3-CDR3-FR4$_{T\text{-}kappa}$-C$_{T\text{-}Kappa}$ |
| AVD 5: | FR1$_{T\text{-}Lambda}$-CDR1-FR2-CDR2-FR3-CDR3-FR4-C$_{T\text{-}Lambda}$ |
| AVD 6: | FR1$_{T\text{-}Kappa}$-CDR1-FR2-CDR2-FR3-CDR3-FR4-C$_{T\text{-}Lambda}$ |
| AVD 7: | FR1$_{T\text{-}Lambda}$-CDR1-FR2-CDR2-FR3-CDR3-FR4-C$_{T\text{-}Kappa}$ |

TABLE 1-continued

| | |
|---|---|
| AVD 8: | FR1$_{T\text{-}kappa}$-CDR1-FR2-CDR2-FR3-CDR3-FR4-C$_{T\text{-}Kappa}$ |
| AVD 9: | FR1$_{T\text{-}Lambda}$-CDR1-FR2-CDR2-FR3-CDR3-FR4$_{T\text{-}Lambda}$-C$_{T\text{-}Lambda}$ |
| AVD 10: | FR1$_{T\text{-}kappa}$-CDR1-FR2-CDR2-FR3-CDR3-FR4$_{T\text{-}kappa}$-C$_{T\text{-}Kappa}$ |

AVD = Antibody Variable Domain; T = Target species; Lambda = lambda light chain; Kappa = kappa light chain; C = Constant domain; FR = Framework region; CDR = Complementarity Determining Region.

II. Antibody Heavy Chains Domains

Illustrated below in Table 2, are diagrammatic representations of the heterochimerization for the heavy chains, showing contiguous sequences of discrete immunoglobulin domains. Abbreviations are as above in EXAMPLE 1.1.

TABLE 2

| | |
|---|---|
| AVD 11: | FR1-CDR1-FR2-CDR2-FR3-CDR3-FR4$_T$-C$_T$ |
| AVD 12: | FR1$_T$-CDR1-FR2-CDR2-FR3-CDR3-FR4-C$_T$ |
| AVD 13: | FR1$_T$-CDR1-FR2-CDR2-FR3-CDR3-FR4$_T$-C$_T$ |

III. Framework Sequences

Exemplary framework sequences (FR4) used as a source to construct the light chain heterochimeric antibodies and/or fragments thereof are provided in the sequence listing as SEQ ID NOs:1-12. In this example, sequences from canine light chains are provided using the Kabat nomenclature.

Exemplary framework sequences (FR4) used as a source to construct the heavy chain heterochimeric antibodies and/or fragments thereof are provided in the sequence listing as SEQ ID NOs:13-19. The standard abbreviations for amino acid residues are used to list the sequences.

Exemplary framework sequences (FR1) used as a source to construct the light chain heterochimeric antibodies and/or fragments thereof are provided in the sequence listing as SEQ ID NOs:20-25.

Exemplary framework sequences (FR1) used as a source to construct the heavy chain heterochimeric antibody and/or fragments thereof are provided in the sequence listing as SEQ ID NOs: 26-40.

EXAMPLE 2

Construction, Expression and Purification of Antibody Variants

I. Antibody Variants Derived from the Rat Anti-human CD52 Antibody

The rat anti-human CD52 antibody was caninized according to the present invention. The sequence of the anti-human CD52 antibody as described in pdb 1bfo_E and pdb 1bfo_F (Campath-1G, clone YTH 34.5HL, Protein Data Bank proteins (pdb), date of deposition: May 20, 1998). Variable regions were prepared by assembling synthetic oligonucleotides corresponding to the publically available sequence, and cloned into pSMART with HindIII and NheI as flanking restriction sites on the 5'- and 3'-end of the variable domains, respectively. Assembled products were then subcloned into an expression vector containing a promoter and the heavy chain constant domain or containing the lambda light chain constant domain. The entire expression cassette included the human cytomegalovirus immediate-early (CMV) promoter, a kozak sequence and signal peptide sequence immediately upstream of the coding sequence and in frame with the variable region of both the light and heavy chains to direct the resulting antibody product towards the secretory pathway.

Antibody variants containing canine sequences were constructed using the rat anti-human CD52 variable regions as template. In this example, the canine sequences were compiled from genomic sequences available at the National Center for Biotechnology Information (NCBI) and sequences with high occurrence were selected to construct the genes of the present example. The CDR domains, the framework regions and the J fragments were identified as described by Kabat and modified as listed in Table 3. The modified expression cassettes containing the various combinations were linked to canine constant regions listed in the present invention. These antibody variant genes were then transferred to expression vectors for production of recombinant antibodies in mammalian cells.

VET111 contained the rat kappa variable domain sequence in its entirety linked to a canine lambda constant domain of VET104. In VET114, the rat kappa J fragment was replaced by a canine lambda J fragment. In VET112, both the rat kappa J fragment and the rat kappa FR1 were replaced with canine lambda sequences. VET222 contained the rat heavy chain variable domain in its entirety linked to the canine constant domain of VET214. In VET 224, the rat J fragment was replaced by a canine J fragment. In VET223, both the rat J fragment and the rat FR1 were replaced with canine sequences.

gen) according to the manufacturer's instructions. The immunoglobulin heavy chain variable region (VH) and the immunoglobulin light chain variable region (VK) were amplified by PCR using primers described previously (O'Brien & Jones, 40: 567-592 (2001)). The PCR reactions were set as recommended by the manufacturer (Invitrogen) The samples were denatured at 94° C. for 5 min followed by amplifications for 35 cycles (94° C. for 30 s, 55° C. for 20 s, 72° C. for 45 s). The variable domains were then amplified with primers containing the HindIII and NheI restriction sites to allow for the cloning of the PCR product into the corresponding restriction sites of expression vectors. Amino acid sequence of the murine anti canine lymphoma monoclonal antibody are listed as SEQ ID NO:47 for the heavy chain and SEQ ID NO:48 for the light chain.

Antibody variants containing canine sequences were constructed using the murine anti-canine lymphoma antibody mab 231 variable regions as template. In this example, the canine sequences were compiled from expressed sequences available at the National Center for Biotechnology Information (NCBI) and sequences with high occurrence were selected to construct the genes of the present example. The CDR domains, the framework regions and the J fragments were identified as described by Kabat and modified as listed in Table 4. The modified expression cassettes containing the various combinations were linked to canine constant regions listed in the present invention. These composite antibody

TABLE 3

| Designation | Structure | SEQ ID NO: |
|---|---|---|
| Light Chain | | |
| VET111 | $FR1_{R\text{-}VK}\text{-}CDR1_{R\text{-}VK}\text{-}FR2_{R\text{-}VK}\text{-}CDR2_{R\text{-}VK}\text{-}FR3_{R\text{-}VK}\text{-}CDR3_{R\text{-}VK}\text{-}FR4_{R\text{-}VK}\text{-}C_{D\text{-}L}$ | 41 |
| VET112 | $FR1_{D\text{-}VL}\text{-}CDR1_{R\text{-}VK}\text{-}FR2_{R\text{-}VK}\text{-}CDR2_{R\text{-}VK}\text{-}FR3_{R\text{-}VK}\text{-}CDR3_{R\text{-}VK}\text{-}FR4_{D\text{-}VL}\text{-}C_{D\text{-}L}$ | 42 |
| VET114 | $FR1_{R\text{-}VL}\text{-}CDR1_{R\text{-}VK}\text{-}FR2_{R\text{-}VK}\text{-}CDR2_{R\text{-}VK}\text{-}FR3_{R\text{-}VK}\text{-}CDR3_{R\text{-}VK}\text{-}FR4_{D\text{-}VL}\text{-}C_{D\text{-}L}$ | 43 |
| Heavy Chain | | |
| VET222 | $FR1_{R\text{-}VH}\text{-}CDR1_{R\text{-}VH}\text{-}FR2_{R\text{-}VH}\text{-}CDR2_{R\text{-}VH}\text{-}FR3_{R\text{-}VH}\text{-}CDR3_{R\text{-}VH}\text{-}FR4_{R\text{-}VH}\text{-}C_{D\text{-}H}$ | 44 |
| VET223 | $FR1_{D\text{-}VH}\text{-}CDR1_{R\text{-}VH}\text{-}FR2_{R\text{-}VH}\text{-}CDR2_{R\text{-}VH}\text{-}FR3_{R\text{-}VH}\text{-}CDR3_{R\text{-}VH}\text{-}FR4_{D\text{-}VH}\text{-}C_{D\text{-}H}$ | 45 |
| VET224 | $FR1_{R\text{-}VH}\text{-}CDR1_{R\text{-}VH}\text{-}FR2_{R\text{-}VH}\text{-}CDR2_{R\text{-}VH}\text{-}FR3_{R\text{-}VH}\text{-}CDR3_{R\text{-}VH}\text{-}FR4_{D\text{-}VH}\text{-}C_{D\text{-}H}$ | 46 |

R: Rat; D: Dog; $FR_{R\text{-}VK}$ = Rat kappa light chain (LC) FR; $FR_{D\text{-}VL}$ = Canine lambda LC FR; $CDR_{R\text{-}VK}$ = Rat kappa LC CDR; $CDR_{R\text{-}VH}$ = CDR from a rat heavy chain (HC); $CD_{D\text{-}L}$ or $CD_{D\text{-}K}$ = Constant domain from a canine lambda or canine kappa LC; $CD_{D\text{-}H}$ = Constant domain from canine HC.

II. Antibody Variants Derived from a Murine Anti-Canine Lymphoma Antibody

The heavy and light chains of the murine anti-canine lymphoma monoclonal antibody mab 231 were isolated from hybridoma cells (ATCC Number: HB-9401). Briefly, total RNA was extracted from 1 million hybridoma cells using the MasterPure™ RNA Purification Kit (Epicentre Biotechnology). The first-strand cDNA was synthesized from 1 μg of total RNA using SuperScript System for RT-PCR (Invitrogenes were then transferred to expression vectors for production of recombinant antibodies in mammalian cells.

The murine kappa variable domain in its entirety was either linked to a canine lambda constant domain of VET104 or to a canine kappa constant domain of VET105. In VET 118, the murine kappa J fragment (or FR4) was replaced by a canine kappa J fragment. VET217 contained the murine heavy chain variable domain in its entirety linked to the canine constant domain of VET214. In VET 218, the murine J fragment was replaced by a canine J fragment.

TABLE 4

List of anti-canine lymphoma antibody variants.

| Designation | Structure | SEQ ID NO: |
|---|---|---|
| Light Chain | | |
| VET106 | $FR1_{M\text{-}VK}\text{-}CDR1_{M\text{-}VK}\text{-}FR2_{M\text{-}VK}\text{-}CDR2_{M\text{-}VK}\text{-}FR3_{M\text{-}VK}\text{-}CDR3_{M\text{-}VK}\text{-}FR4_{M\text{-}VK}\text{-}C_{D\text{-}L}$ | 49 |
| VET107 | $FR1_{M\text{-}VK}\text{-}CDR1_{M\text{-}VK}\text{-}FR2_{M\text{-}VK}\text{-}CDR2_{M\text{-}VK}\text{-}FR3_{M\text{-}VK}\text{-}CDR3_{M\text{-}VK}\text{-}FR4_{M\text{-}VK}\text{-}C_{D\text{-}K}$ | 50 |
| VET118 | $FR1_{M\text{-}VK}\text{-}CDR1_{M\text{-}VK}\text{-}FR2_{M\text{-}VK}\text{-}CDR2_{M\text{-}VK}\text{-}FR3_{M\text{-}VK}\text{-}CDR3_{M\text{-}VK}\text{-}FR4_{D\text{-}VL}\text{-}C_{D\text{-}L}$ | 51 |

TABLE 4-continued

List of anti-canine lymphoma antibody variants.

| Designation | Structure | SEQ ID NO: |
|---|---|---|
| | Heavy Chain | |
| VET217 | FR1$_{M\text{-}VH}$-CDR1$_{M\text{-}VH}$-FR2$_{M\text{-}VH}$-CDR2$_{M\text{-}VH}$-FR3$_{M\text{-}VH}$-CDR3$_{M\text{-}VH}$-FR4$_{M\text{-}VH}$-C$_{D\text{-}H}$ | 52 |
| VET218 | FR1$_{M\text{-}VH}$-CDR1$_{M\text{-}VH}$-FR2$_{M\text{-}VH}$-CDR2$_{M\text{-}VH}$-FR3$_{M\text{-}VH}$-CDR3$_{M\text{-}VH}$-FR4$_{D\text{-}VH}$-C$_{D\text{-}H}$ | 53 |

M: Mouse; D: Dog; FR$_{M\text{-}VK}$ = Murine kappa LC FR; FR$_{D\text{-}VL}$ = FR Canine lambda LC FR; CDR$_{M\text{-}VK}$ = Murine kappa LC CDR; CDR$_{M\text{-}VH}$ = Murine HC CDR; CD$_{D\text{-}L}$ or CD$_{D\text{-}K}$ = Constant domain from a canine lambda or canine kappa LC; CD$_{D\text{-}H}$ = Constant domain from a canine HC.

III. Cloning of Canine Heavy and Light Chain Constant Domains

Heavy chain and light chain sequences were cloned from cDNA made from canine peripheral blood (PBMC) or from canine spleen tissues. The coding regions or fragment thereof were then amplified by PCR using the primers listed below. The PCR reactions were set as recommended by the manufacturer (Invitrogen). The samples were denatured at 94° C. for 5 min followed by amplifications for 35 cycles (94° C. for 30 s, 62° C. for 20 s, 72° C. for 45 s). The PCR products were first cloned into a pUC-derived vector. The genes were then re-amplified with flanking restriction sites for cloning into pcDNA3-derived vector (Invitrogen). The Heavy chain was amplified with primers listed as SEQ ID NO:57 and SEQ ID NO:58; the lambda light chain was amplified with primers listed as SEQ ID NO:59 and SEQ ID NO:60; and the lambda light chain was amplified with primers listed as SEQ ID NO:61 and SEQ ID NO:62. The amino acid sequence of the heavy chain is listed as SEQ ID NO:54 (Plasmid VET214); the amino acid sequence of the lambda light chain is listed as SEQ ID NO:55 (Plasmid VET104); and the amino acid sequence of the kappa light chain is listed as SEQ ID NO:56 (Plasmid VET105).

IV. Expression, Purification and Quantitation of Antibody Variants

Genes were assembled from synthetic oligonucleotides and cloned into HindIII-NheI the cloning sites of an expression vector deriving from pcDNA3 containing a leader sequence allowing for the secretion of the antibody molecule, a Kozak sequence, the canine constant domain region, and a terminal codon. The light chain variable domains were cloned either into VET104 or VET105. The heavy chain variable domains were cloned into VET214.

These plasmids were transformed into *E. coli* (DH5a) chemically competent *E. coli* cells (Lucigen), grown in Luria Broth (LB) media and stocked in glycerol. Large scale plasmid DNA was prepared using the Zyppy™ Plasmid Maxiprep Kit as described by the manufacturer (Zymo Research Corp.). The antibody variants were transiently expressed in the human embryonic kidney cell line 293F (Invitrogen) in serum-free condition. The heavy chain (VET200 series) and light chain (VET100 series) expression vectors were co-transfected using 293fectin (Invitrogen) and grown in 293F-FreeStyle culture medium (Invitrogen). The transfected 293 cultures expressed approximately 3-12 mg/L of recombinant antibody. Binding assays were performed with supernatants or with recombinant antibodies purified from supernatants.

The antibody titer was determined using a quantitative ELISA. Plates were coated with 100 ul/well at 37° C. for 1 hour with rabbit anti-dog IgG (H+L) antibody (Jackson Immuno-Research) diluted 1:100 in carbonate buffer (100 mM NaHCO$_3$, 33.6 mM Na$_2$CO$_3$, pH 9.5). The plates were washed three times with TBS-T (50 mM Tris, 0.14 M NaCl, 0.05% tween-20, pH 8.0) and blocked with 200 ul/well TBS/BSA (50 mM Tris, 0.14 M NaCl, 1% BSA, pH 8.0) for 1 hour at 37° C. The standard was prepared by diluting the reference antibody (Jackson Immuno-Research, Dog Gamma Globulin 10.0 mg) in TBS-T/BSA (TBS-T, 1% BSA) in a range of concentration from 0 to 500 ng/ml. After washing the plates twice with TBS-T, standard/samples preparation was added to each well and incubated at 37° C. for 1 hour. The plates were then washed 3× with TBS-T and incubated for 1 hour at 37° C. with HRP-rabbit anti-dog IgG antibody (Perodixase Rabbit Anti-Dog IgG (H+L) Jackson Immuno-Research) diluted 1:20,000 in TBS-T/BSA. The plates were washed twice with TBS-T and developed using 100 ul/well of TMB substrate. The reaction was stopped with 1M H$_2$SO$_4$ and the OD was measured at 450 nm. The standard curve was fitted using a four parameter equation and used to calculate the antibody concentration in the samples.

Antibodies were purified from culture supernatants using protein A affinity chromatography. Supernatants were diluted 1:1 with Binding Buffer (Pierce) and passed over a gravity-flow column (GE Healthcare), equilibrated with 20 resin-bed volumes of Binding Buffer. The antibody retained on the column was washed with 15 ml of binding buffer, eluted with low pH elution buffer (Pierce) and collected in 1 ml fractions containing 100 ul of Binding Buffer to neutralize the pH. Fractions with absorbance (280 nm)>0.1 were desalted using desalting columns (Pierce). The purity of each preparation was assessed by HPLC and was determined to be over 95% by standard techniques. The purity of all the antibody preparation was examined by HPLC (High Pressure Liquid Chromatography). All the variants exhibited a similar elution pattern consisting of a major peak detected by absorbance at 280 nm at a position similar than the standard control. There was no significant aggregation detected by gel filtration.

EXAMPLE 5

Binding of Antibody Variants to Cells

I. Antibody Variants to CD52 Bind Tumor Cells

The binding of the antibody variants of the present invention was assessed using a fluorescence-activated cell sorter (FACS). In the present example, the antibody variants were incubated with the CD52 positive cells and the amount of bound antibody was assessed following incubation with a fluorescent-labeled reporter reagent. The reporter was thereafter measured by FACS.

Briefly, for each assay, one million cells of the human T-cell lymphoma HUT-78 cells were resuspended in FACS buffer (PBS+2% FBS). About 2 ug of the primary antibody were added to the cells and the samples were incubated at 4° C. for 1 hour. The primary antibody was provided as supernatants from transfected cells with recombinant antibody constructs or from purified antibody preparation. The rat anti-human CD52 mAb (Serotec) was added to the cells as a control. One ml of FACS buffer was added and cells were spin down for 3 min at 800×g in Eppendorf microcentrifuge. The cells were washed with 1 ml FACS buffer and spin down again. The secondary antibodies such as fluorescein-isothiocynate (FITC) conjugated goat anti-rat (Jackson ImmunoResearch), or the FITC-conjugated goat anti-dog IgG (H+L) (Bethyl Laboratories) were added in 100 µl of FACS buffer supplemented with 1% BSA to appropriate tubes and the tubes were incubated at 4° C. for 30 minutes. The wash steps were repeated. The cells were then resuspended in 500 µl FACS buffer and transferred into 12×75 mm polystyrene test tubes. The cells were analyzed by FACS with a FacScan cytometer using the CellQuest software (Becton-Dickenson). Several controls were utilized to determine the background fluorescence: (i) one tube of cells was incubated with the FITC-conjugated secondary antibody without the primary antibody, (ii) one tube of cells was incubated with PBS only, and (iii) one tube was incubated with the primary antibody without the FITC-conjugated secondary antibody.

A typical staining profile is reported in Table 5. The results of Table 5 evidence effective binding of the chimeric antibody (VET111 VET222) and of the antibody variants.

TABLE 5

Combinations of antibody variants tested by FACS analysis for their binding to CD52 positive lymphoma cells.

| Conditions | Binding (%) |
|---|---|
| Cells only | 1.09 |
| Cells + anti-dog IgG | 4.65 |
| Cells + anti-rat IgG | 1.15 |
| Cells + VET 111 VET 222 | 0.88 |
| Cells + VET 112 VET 223 | 0.88 |
| Cells + VET 114 VET 224 | 0.68 |
| Cells + VET 112 VET 224 | 0.89 |
| Cells + VET 114 VET 223 | 0.95 |
| Cells + rat anti-human CD52 | 1.36 |
| Cells + VET 111 VET 222 + anti-dog IgG | 51.40 |
| Cells + VET 112 VET 223 + anti-dog IgG | 24.35 |
| Cells + VET 114 VET 224 + anti-dog IgG | 47.77 |
| Cells + VET 112 VET 224 + anti-dog IgG | 30.60 |
| Cells + VET 114 VET 223 + anti-dog IgG | 40.08 |
| Cells + rat anti-human CD52 + anti-rat IgG | 41 |

II. Anti-Canine Lymphoma Antibody Variants Bind Tumor Cells

The binding of the antibody variants of the present invention were testing on canine lymphoma cells by FACS. In the present example, the different antibody variants were incubated with canine lymphoma cells positive for the target antigen of mab 231 and the amount of bound antibody was assessed following incubation with a fluorescent-labeled reporter reagent. The reporter was thereafter measured by FACS.

The binding assay was performed as described above. A typical staining profile obtained with the variants is reported in Table 6. These results evidence effective binding of the various variants.

TABLE 6

Combination of antibody variants tested by FACS analysis for their binding to cells.

| Conditions | Binding (%) |
|---|---|
| Cells only | 1.05 |
| Cells + anti-dog IgG | 4.19 |
| Cells + anti-mouse IgG | 3.13 |
| Cells + VET 106 VET 217 | 1.51 |
| Cells + VET 107 VET 217 | 1.25 |
| Cells + VET 118 VET 218 | 1.64 |
| Cells + mab 231 | 1.49 |
| Cells + VET 106 VET 217 + anti-dog IgG | 30.32 |
| Cells + VET 107 VET 217 + anti-dog IgG | 20.82 |
| Cells + VET 118 VET 218 + anti-dog IgG | 27.20 |
| Cells + mab 231 + anti-mouse IgG | 74.21 |

III. Anti-CD52 Antibody Variants Alter Proliferation of Tumor Cells

The antibody variants of the present invention were tested for their ability to alter proliferation of lymphoma cells.

Lymphoma cells were grown in RPMI medium with FBS 10% in 5% carbon dioxide ($CO_2$) at 37° C. Cells were seeded at 5,000 cells/well in 96-well plates in medium with 2.5% FBS. Cells were treated with the antibody variants or the rat or dog isotype controls (10 µg/ml) and incubated for 72 h at 37° C. in a $CO_2$ incubator. Ten (10) µl MTT solution was added to each well and incubated at 37° C. for 4 h according to the manufacturer's instruction (Trevigen). Optical density (OD) was then measured at 490 nm and data are presented as means±S.D. of three replicate measurements. The data illustrate in Table 7 that the antibody variants had an anti-proliferative effect on lymphoma cells similar than the rat anti-human CD52 antibody.

TABLE 7

Proliferation cell assay with antibody variants and controls.

| Conditions | Average ± SD |
|---|---|
| Cells | 0.486 ± 0.028 |
| Rat Isotype | 0.488 ± 0.043 |
| Dog Isotype | 0.479 ± 0.045 |
| VET111 VET222 | 0.213 ± 0.012 |
| VET 114 VET 224 | 0.246 ± 0.012 |
| Rat anti-human CD52 | 0.259 ± 0.020 |

EXAMPLE 6

Anti-CD52 Antibody Variants Alter Proliferation of Tumor Cells

The antibody variants of the present invention were tested for their ability to alter proliferation of lymphoma cells.

Lymphoma cells were grown in ISCOVE medium with FBS 20% in 5% carbon dioxide ($CO_2$) at 37° C. Cells were seeded at 5,000 cells/well in 96-well plates in medium with 2.5% FBS. Cells were treated with the antibody variants or the isotype control (10 µg/ml) and incubated for 72 h at 37° C. in a $CO_2$ incubator. Ten (10) µl MTT solution was added to each well and incubated at 37° C. for 4 h according to the manufacturer's instruction (Trevigen). Optical density was then measured at 490 nm. Data are presented as means±S.D. of three replicate measurements. The percentage survival was expressed relative to the non-treated controls which were defined as 100%. The data illustrate in Table 8 that the modified antibody variants had an anti-proliferative effect on lymphoma cells.

TABLE 8

Proliferation cell assay with antibody variants
and controls (PI: Proliferation Inhibition in %).

| Conditions | PI (%) 10 ug/ml |
|---|---|
| VET 111 VET 222 | |
| Rat anti-human CD52 | |
| Rat Isotype | |
| Dog Isotype | |

EXAMPLE 7

Antibody to CD20

I. Cloning of Canine and Feline CD20

Ia. Cloning of Canine CD20 gene. The canine CD20 gene was cloned into a mammalian expression vector and the corresponding plasmid DNA was transfected into mammalian cells to produce a properly folded form of the receptor. Cells expressing CD20 were used for immunization and cell-screening based assays.

CD20 was isolated from canine peripheral blood mononuclear cells (PBMC). Total RNA was extracted from 1 million canine peripheral blood mononuclear cells (PBMC) using the MasterPure™ RNA Purification Kit (Epicentre Biotechnology). The first-strand cDNA was synthesized from 2 μg of total RNA using SuperScript, First-Strand Synthesis, System for RT-PCR kit (Invitrogen) according to the manufacturer's instructions. The coding region was amplified with primers of SEQ ID NO: 63 and SEQ ID NO: 64 and a fragment thereof encompassing the large extracellular domain (loop) was amplified with primers of SEQ ID NO: 65 and SEQ ID NO: 66 by PCR. The PCR reactions were set as recommended by the manufacturer (Invitrogen). The samples were denatured at 94° C. for 5 min followed by amplifications for 35 cycles (94° C. for 30 s, 62° C. for 20 s, 72° C. for 45 s) and the PCR products were cloned into pcDNA-derived vector (Invitrogen).

The amino-acid sequence of the canine CD20 isolated from canine PBMC is listed as
SEQ ID NO 67.

Ib. Cloning of Feline CD20 Gene. The feline CD20 coding region was isolated from feline peripheral blood mononuclear cells (PBMC) fractionated from whole blood. Total RNA was extracted from 5 million feline peripheral blood mononuclear cells (PBMC) using the Mini RNA Isolation Kit (Zymo Research). The first-strand cDNA was synthesized from 2 μl of total RNA using SuperScript, First-Strand Synthesis System for RT-PCR kit according to the manufacturer's instructions. The coding region was then amplified by PCR using the primers of SEQ ID NO:63 and SEQ ID NO:68 using GoTaq Green Master Mix according to manufacturer's instructions. The samples were denatured at 94° C. for 5 min followed by amplifications for 35 cycles (94° C. for 30 s, 52° C. for 30s, 72° C. for 1 min). The PCR products were then cloned into pJET 1.2 (Fermentas) and transformed into E. coli strain DH5a and sequenced to verify PCR specificity.

The amino-acid sequence of the canine CD20 isolated from feline PBMC is given as
SEQ ID NO:69.

The feline CD20 gene or fragment thereof is used for immunization to generate antibodies. The immunogen is a plasmid carrying the feline CD20 DNA sequence or a fragment thereof, the CD20 protein or a fragment thereof or a cell line naturally expressing CD20 or transfected with the CD20 gene or a fragment thereof;

The feline CD20 gene or fragment is used to design peptides or is expressed in cells to be used for screening assays.

II. Epitope Prediction for Canine CD20 Amino Acid Sequence

The epitope prediction was assessed for the amino acid sequence of the canine CD20 isolated above by using the prediction algorithm Emboss available online (http://liv.bm-c.uu.se/cgi-bin/emboss/antigenicc). This algorithm scores the antigenicity potential of a given sequence. This program predicts four potential epitopes to be exposed at the surface of cells comprising residues 74-84, 178-188, 154-170, or 140-146 of SEQ ID NO:69. At least six additional sequences were predicted as potential epitopes based on hydrophilicity, flexibility, accessibility, turns, exposed surface, and polarity of polypeptides chains using other algorithms available on line (http://tools.immuneepitope.org) comprising residues 162-173, 148-159, 142-153, 148-169, 166-177, 161-176 of SEQ ID NO:67.

The epitopes recognized by the anti-CD20 antibodies are discontinuous, comprising regions from both extracellular loops.

III. Immunization with CD20 and Generation of Murine Monoclonal Antibodies to Canine CD20

To generate monoclonal antibodies to canine CD20, CHO-DG44 (Chinese hamster ovary cells, dihydrofolate reductase deficient ATCC CRL-9096) and NIH:3T3 (ATCC CRL-1658) were transfected with an expression vector encoding the full-length canine CD20 protein such that the protein was expressed on the surface of the cells. Magnetic Proteoliposome Particles (MPLs) containing CD20, such that the native conformation of the transmenbrane receptor is maintained were prepared for immunizations and panning. In brief, recombinant canine CD20 that contained an epitope tag was solublized from a transfected CD20-expressing cell line using the detergent CHAPSO and the protein was captured on magentic beads via the epitope tag. A lipid membrane was reconstituted during removal of the detergent, such that the native membrane conformation of CD20 was maintained, to create the CD20-MPLs.

Anti-CD20 monoclonal antibodies were generated by immunization of mice to raise immunoglobulins specific for canine CD20. Washed CHO-DG44 cells expressing canine CD20 ($1 \times 10^7$ cells in 100 ul) or 100 ul of CD20-MPLs ($1 \times 10^9$ beads/ml) were used as immunogens. Mice were immunized with antigen in Ribi adjuvant intraperitonealy three times, then boosted twice on consecutive days. The immune response was monitored by retro-orbital bleeds. The sera were screened by FACS staining of CD20-expressing cells (versus untransfected parental cells) and CD20-MPLs.

Mice with sufficient titers of anti-CD20 immunoglobulin were used for harvesting spleens. A murine antibody library was prepared from spleen cells of the mice and displayed on phage such that the phage were then screened for expression of antibodies with specificity for CD20. This combination approach is generally described in U.S. Pat. No. 6,092,098.

The phage display library was screened for library members having affinity for CD20 by panning with canine CD20 incorporated into magnetic proteoliposomes (CD20-MPL). Three rounds of panning of the phage display library on the CD20-MPLs led to several fold enrichment of CD20-binders as compared to background. Variable region fragments of interest were recloned into a Fab expression vector and the Fab retested for antigen binding against transfected CD20-expressing cells.

IV. Anti-CD20 Antibody Leads

A lead candidate with high affinity for the canine CD20 exhibiting efficacy is identified by testing it in a panel of assays using methodologies available to those in the art.

The specific binding of the newly generated anti-CD20 antibodies is assessed by ELISA and FACS with cells expressing CD20. Since it is important to measure the relative binding affinity of the antibodies to native CD20, live cells expressing CD20 are used and ELISA and FACS analysis. For cell-binding assay, CD20 expressing cells or canine lymphoma cells are washed with phosphate-buffered saline (PBS) and seeded in well. After one hour at room temperature to allow cell attachment to the plate surface, the cells are washed with FBS to block non-specific binding sites on the plates. Supernatants from cells expressing the anti-canine CD20 are then added. After one hour incubation at room temperature, the plates are washed with PBS. The secondary antibody is then added and detected using standard procedures.

Alternatively, a peptide-based ELISA starting from a linear peptide containing the residues encompassing the extracellular domain of CD20 is designed. Additional conformational modifications can be made to improve peptide recognition and/or epitope presentation. The modifications may include addition of carbohydrate, addition of residues to form a disulfide bond or to cross-link a carrier protein.

Alternatively, whole blood from dogs is collected in sodium heparin tubes, then incubated with the anti-CD20 antibody and the binding of the anti-CD20 antibody to certain desirable cells are analyzed by FACS.

Additional biophysical properties such as affinity, thermostability are determined using methodologies available to those in the art.

To assess the ability of anti-CD20 antibody to augment the cytotoxic effects of chemotherapeutic drugs, the antibody is tested in a chemosensitization assay using methodologies available to those in the art.

A tumor killing assay is developed to measure the effect of the recombinant antibody on various canine tumor cells lines.

An in vitro apoptosis assay is developed to measure the loss of plasma membrane integrity in canine CD20 positive cells after anti-CD20 antibody treatment by staining with Annexin V and Propidium Iodide. This assay is used to assess the ability of anti-CD20 antibodies to induce apoptosis.

CDC is an important effector mechanism in the removal of tumor cells in vivo. The complement system has three parts, the classical, lectin, and alternative pathways. The classical pathway is activated by antibodies bound to target antigens and therefore relevant to tumor cell removal after therapeutic antibody treatment, while the lectin and alternative pathways target microbes. The first step in activation of the classical pathway is binding of the C1q component to the Fc portions of antibodies. This triggers a proteolytic cascade that ultimately leads to target cell death by direct disruption of the plasma membrane, or by effector cell mediated killing through component C3b binding to receptors on NK cells or macrophages. A CDC assay is developed to assess the degree of complement activation and tumor killing exhibited by the anti-CD20 antibodies. CD20 positive canine cells are incubated with anti-CD20 antibodies and canine complement components. Cell viability will then be detected by a fluorescent assay.

ADCC assays are conducted with fresh canine PBMC from normal donors and diseased donors. Target cells are $^{51}$Cr-labeled by incubation with 250 µCi of $^{51}$Cr for 2 h at 37° C. Then, antibodies and canine PBMC are added to the wells to assure effector to target ratios of 50:1, 25:1, 10:1, and 2:1 with the addition of 5,000 target cells to each well. Each condition is performed in triplicate and the plates are incubated for 4 hours at 37° C. Maximal release of $^{51}$Cr from tumor cells is established by culturing targets with detergent. Effector and target cells are co-cultured overnight, at which time cell-free supernatants are harvested to measure the level of $^{51}$Cr released in supernatants. The % cytotoxicity is determined using the formula: (Experimental cpm count−Spontaneous cpm count)/(Maximal cpm count−Spontaneous cpm count). Spontaneous release represents the radioactivity of culture supernatants from the target cells alone, maximal count measures the radioactivity of supernatants from target cells lysed with detergent, and experimental release the radioactivity measured in supernatants from wells containing targets plus effector cells.

The anti-CD20 antibody is rapidly evaluated in lymphoma xenograft murine models using CD20-positive canine tumor cell lines according to methodologies available to those in the art.

V. Engineering of the Modified Anti-CD20 Antibody

As the anti-CD20 monoclonal antibodies generated in a non-canine mammal, most may not be suitable for repeated administration, the corresponding chimeric or caninized antibody is generated as described in Example 1 and tested for a panel of properties as described in the Example above.

VI. Depletion of B Cells in Vivo Using Anti-CD20

To ascertain the efficacy of anti-CD20 antibody in depleting B cells in vivo, dogs are treated with single or consecutive dose levels ranging from 0.1 mg/kg to 5 mg/kg. Dogs ranging in weight from 2.5 to 5 kilograms are divided into three groups of two dogs each. All animals are injected with anti-CD20 antibody produced from mammalian cells. The three groups received antibody dosages corresponding to 0.1 mg/kg, 0.5 mg/kg, and 5 mg/kg each day for four (4) consecutive days by intravenous infusion; blood samples are drawn prior to each infusion. Additional blood samples are drawn beginning 24 hrs after the last injection (T=O) and thereafter on days 1, 3, 7, 14 and 28.

Approximately 5 ml of whole blood from each animal is centrifuged at 2000 RPM for 5 min. Plasma is removed for assay of soluble anti-CD20 antibody levels. The pellet (containing peripheral blood leukocytes and red blood cells) is resuspended in fetal calf serum for FACS analysis.

For the labeling of leukocytes, cells are washed twice with Hanks Balanced Salt Solution ("HBSS") and resuspended in a plasma equivalent volume of fetal bovine serum (FBS). A Fluorescein labeled monoclonal antibodies with specificity for the lymphocyte surface markers of B-cell and T-cell are added to identify T and B lymphocyte populations. Cells are incubated with fluorescent antibodies for 30 min., washed and analyzed on a Becton Dickinson FACScan instrument. Lymphocyte populations are initially identified by forward versus right angle light scatter in a dot-plot bitmap with unlabeled leucocytes. The total lymphocyte population is then isolated by gating out all other events.

VII. Treatment of Dogs

A dog diagnosed with a condition including lymphoma, relapsed lymphoma, leukemia, hemolytic anemia, arthritis, atopic dermatitis is given therapy with the anti-CD20 monoclonal antibody. The dog is infused intravenously, intraperitoneally, or subcutaneously with 5 mg/kg of antibody, and the treatment is repeated weekly for 4-8 weeks following the initial treatment. Two months after the final dose, the patient shows reduced levels of certain types of cells expressing CD20.

VIII. Treatment of Cats

A cat diagnosed with a condition including lymphoma, relapsed lymphoma, leukemia, hemolytic anemia, arthritis, atopic dermatitis is given therapy with the anti-CD20 monoclonal antibody. The cat is infused intravenously or subcutaneously with 5 mg/kg of antibody, and the treatment is repeated weekly for 4-8 weeks following the initial treatment. Two months after the final dose, the patient shows reduced levels of certain types of cells expressing CD20.

IX. Treatment of Horses

A horse diagnosed with a condition including lymphoma, relapsed lymphoma, leukemia, hemolytic anemia, arthritis, atopic dermatitis is given therapy with the anti-CD20 monoclonal antibody. The horse is infused intravenously or subcutaneously with 5 mg/kg of antibody, and the treatment is repeated weekly for 4-8 weeks following the initial treatment. Two months after the final dose, the patient shows reduced levels of certain types of cells expressing CD20.

EXAMPLE 8

Antibodies to CD52

I. Cloning of the Canine CD52 Coding Sequence

CD52 was isolated from canine peripheral blood mononuclear cells (PBMC). Total RNA was extracted from 1 million canine peripheral blood mononuclear cells (PBMC) using the MasterPure™ RNA Purification Kit (Epicentre Biotechnology). The first-strand cDNA was synthesized from 2 µg of total RNA using SuperScript, First-Strand Synthesis, System for RT-PCR kit (Invitrogen) according to the manufacturer's instructions. The coding region or fragment thereof was then amplified by PCR using the primers of SEQ ID NO: 70 and SEQ ID NO: 71. The PCR reactions were set as recommended by the manufacturer (Invitrogen). The samples are denatured at 94° C. for 5 min followed by amplifications for 35 cycles (94° C. for 30 s, 62° C. for 20 s, 72° C. for 45 s). The PCR products are cloned into pcDNA3 (Invitrogen) and sequenced to verify PCR specificity.

The amino-acid sequence of the canine CD52 isolated from canine PBMC is reported as SEQ ID No: 72.

II. Cloning of the Feline CD52 Coding Sequence

The feline CD52 gene was cloned as described above with primers designed to amplify the canine CD52 sequence.

The amino-acid sequence of the feline CD52 isolated from feline PBMC is as follows: SEQ ID NO: 73

III. Epitope Prediction for CD52

The epitope prediction was assessed for the amino acid sequence of the canine CD52 isolated above by using the prediction algorithm Emboss available online (http://liv.bmc.uu.se/cgi-bin/emboss/antigenic). This algorithm scores the antigenicity potential of a given sequence. The program predicts at least five potential epitopes comprising residues 4-18, 20-26, 30-39, 36-47, and 49-64 of SEQ ID NO:72.

IV. Generation of Antibodies to CD52

Antibodies to CD52 are raised using peptides encompassing CD52 amino acid sequences or fragment thereof and using cells expressing CD52 gene or a fragment thereof, selected, engineered and tested analogously to the examples above.

V. Treatment of Dogs

A dog diagnosed with an immune condition including lymphoma, relapsed lymphoma, leukemia, mast cell tumor, hemolytic anemia, arthritis, atopic dermatitis is given therapy with the anti-CD52 monoclonal antibody. The dog is infused intravenously or subcutaneously with 5 mg/kg of antibody, and the treatment is repeated weekly for 4-8 weeks following the initial treatment. Two months after the final dose, the patient shows reduced levels of certain types of cells expressing CD52.

VI. Treatment of Cats

A cat diagnosed with an immune condition including lymphoma, relapsed lymphoma, leukemia, mast cell tumor, hemolytic anemia, arthritis, atopic dermatitis is given therapy with the anti-CD52 monoclonal antibody. The cat is infused intravenously or subcutaneously with 5 mg/kg of antibody, and the treatment is repeated weekly for 4-8 weeks following the initial treatment. Two months after the final dose, the patient shows reduced levels of certain types of cells expressing CD52.

VII. Treatment of Horses

A horse diagnosed with an immune condition including lymphoma, relapsed lymphoma, leukemia, mast cell tumor, hemolytic anemia, arthritis, atopic dermatitis is given therapy with the anti-CD52 monoclonal antibody. The horse is infused intravenously or subcutaneously with 5 mg/kg of antibody, and the treatment is repeated weekly for 4-8 weeks following the initial treatment. Two months after the final dose, the patient shows reduced levels of certain types of cells expressing CD52.

Alternative combinations and variations of the examples provided will become apparent based on this disclosure. It is not possible to provide specific examples for all of the many possible combinations and variations of the embodiments described, but such combinations and variations are nevertheless intended to be within the scope of the invention.

Summary of Sequences Described:

```
Canis FR4 Light Chain (1-12)
FR4LC1    SEQ ID NO 1:    FGGGTHLTVL

FR4LC2    SEQ ID NO 2:    FGSGTPLTVL

FR4LC3    SEQ ID NO 3:    FGAGTKVELIR

FR4LC4    SEQ ID NO 4:    FGQGTRLEVRR

FR4LC5    SEQ ID NO 5:    FGSGTQLTVL
```

-continued

| | | |
|---|---|---|
| FR4LC6 | SEQ ID NO 6: | FGRGTQLTVL |
| FR4LC7 | SEQ ID NO 7: | FGEGTQLTVL |
| FR4LC8 | SEQ ID NO 8: | FGGGTKLEIK |
| FR4LC9 | SEQ ID NO 9: | FGKGTHLEIK |
| FR4LC10 | SEQ ID NO 10: | FGQGTKVEIK |
| FR4LC11 | SEQ ID NO 11: | FGQGTKLEIK |
| FR4LC12 | SEQ ID NO 12: | FGAGTKVEIK |

Canis FR4 Heavy Chain (13-19)
| | | |
|---|---|---|
| FR4HC1 | SEQ ID NO 13: | WGQGTLVTVSS |
| FR4HC2 | SEQ ID NO 14: | WGQGALVTVSS |
| FR4HC3 | SEQ ID NO 15: | WGPGTSLFVSS |
| FR4HC4 | SEQ ID NO 16: | WGLGTLVTVSS |
| FR4HC5 | SEQ ID NO 17: | WGPGTSLFVSS |
| FR4HC6 | SEQ ID NO 18: | WGQGTLVTVSP |
| FR4HC7 | SEQ ID NO 19: | WGQGTTLTVSS |

Canis FR1 Light chain (20-25)
| | | |
|---|---|---|
| FR1LC1 | SEQ ID NO 20: | DIVMTQTPLSLSVSPGEPASISC |
| FR1LC2 | SEQ ID NO 21: | DIVMTQTPLSLSVSPGRPASISC |
| FR1LC3 | SEQ ID NO 22: | DIVMTQTPLSLSVSPGRTASISC |
| FR1LC4 | SEQ ID NO 23: | QSVLTQPASVSGSLGQRVTISC |
| FR1LC5 | SEQ ID NO 24: | QPKASPSVTLFPPSSEELGANKATLVC |
| FR1LC6 | SEQ ID NO 25: | QPKSSPLVTLFPPSSEELGANKATLVC |

Canis FR1 Heavy Chain (26-40)
| | | |
|---|---|---|
| FR1HC1 | SEQ ID NO: 26 | EVQLVESGGDLVKPGGSLRLSCVTS |
| FR1HC2 | SEQ ID NO: 27 | EVQLVESGGNLVKPGGSLRLSCVAS |
| FR1HC3 | SEQ ID NO: 28 | EVQLVESGGDLEKPGGSLRLSCVAS |
| FR1HC4 | SEQ ID NO: 29 | EVQLVESGEDLVKPGGSLRLSCVAS |
| FR1HC5 | SEQ ID NO: 30 | EVQLVESGGDLVKPAGSLRLSCVAS |
| FR1HC6 | SEQ ID NO: 31 | EVQLVESGGDLVKPERSLRLSCVAS |
| FR1HC7 | SEQ ID NO: 32 | EVQLVESGGDLVKPEGSLRLSCVAS |
| FR1HC8 | SEQ ID NO: 33 | EVQLVESGGDLVKPGGTLRLSCVAS |
| FR1HC9 | SEQ ID NO: 34 | EEQLVEFGGHMVNPGGSLGLSCQAS |
| FR1HC10 | SEQ ID NO: 35 | EVQLVESGGDLAKPGGSLRLSCVAS |
| FR1HC11 | SEQ ID NO: 36 | EVQLVESGGDLVKPEGSLRLSCVVS |
| FR1HC12 | SEQ ID NO: 37 | EVQLVQSGAEVKKPGASVKVSCKTS |
| FR1HC13 | SEQ ID NO: 38 | EVQLVESGGDLVKPGGSLRLSCVAS |
| FR1HC14 | SEQ ID NO: 39 | EVQLVESGGDLMKPGGSLRLSCVAS |
| FR1HC15 | SEQ ID NO: 40 | EVQLVESGGDLVKPGGSLRLSCVAF |

| SEQ ID | Structure | Designation | Protein Sequence |
|---|---|---|---|
| Light Chain | | | |
| SEQ ID NO: 41 | FR1$_{R-VK}$-CDR1$_{R-VK}$-FR2$_{R-VK}$CDR2$_{R-VK}$-FR3$_{R-VK}$-CDR3$_{R-VK}$FR4$_{R-VK}$-C$_{D-L}$ | VET111 | DIKMTQSPSFLSASVGDRVTLNCKASQNIDKYLNWYQQKLGESPKLLIYNTNNLQTGIPSRFSGSGSGTDFTLTISSLQPEDVATYFCLQHISRPRTFGTGTKLELK |
| SEQ ID NO: 42 | FR1$_{D-VL}$-CDR1$_{R-VK}$-FR2$_{R-VK}$CDR2$_{R-VK}$-FR3$_{R-VK}$-CDR3$_{R-VK}$FR4$_{D-VL}$-C$_{D-L}$ | VET112 | QSVLTQPASVSGSLGQRVTISCKASQNIDKYLNWYQQKLGESPKLLIYNTNNLQTGIPSRFSGSGSGTDFTLTISSLQPEDVATYFCLQHISRPRTFGGGTHLTV |
| SEQ ID NO: 43 | FR1$_{R-VL}$-CDR1$_{R-VK}$-FR2$_{R-VK}$CDR2$_{R-VK}$-FR3$_{R-VK}$-CDR3$_{R-VK}$FR4$_{D-VL}$-C$_{D-L}$ | VET114 | DIKMTQSPSFLSASVGDRVTLNCKASQNIDKYLNWYQQKLGESPKLLIYNTNNLQTGIPSRFSGSGSGTDFTLTISSLQPEDVATYFCLQHISRPRTFGGGTHLTVL |
| Heavy Chain | | | |
| SEQ ID NO: 44 | FR1$_{R-VH}$-CDR1$_{R-VH}$-FR2$_{R-VH}$CDR2$_{R-VH}$-FR3$_{R-VH}$-CDR3$_{R-VH}$FR4$_{R-VH}$-C$_{D-H}$ | VET222 | EVKLLESGGGLVQPGGSMRLSCAGSGFTFTDFYMNWIRQPAGKAPEWLGFIRDKAKGYTTEYNPSVKGRFTISRDNTQNMLYLQMNTLRAEDTATYYCAREGHTAAPFDYWGQGVMVTVSS |
| SEQ ID NO: 45 | FR1$_{D-VH}$-CDR1$_{R-VH}$-FR2$_{R-VH}$CDR2$_{R-VH}$-FR3$_{R-VH}$-CDR3$_{R-VH}$FR4$_{D-VH}$-C$_{D-H}$ | VET223 | EVQLVESGGDLVKPGGSLRLSCAGSGFTFTDFYMNWIRQPAGKAPEWLGFIRDKAKGYTTEYNPSVKGRFTISRDNTQNMLYLQMNTLRAEDTATYYCAREGHTAAPFDYWGQGTLVTVSS |
| SEQ ID NO: 46 | FR1$_{R-VH}$-CDR1$_{R-VH}$-FR2$_{R-VH}$CDR2$_{R-VH}$-FR3$_{R-VH}$-CDR3$_{R-VH}$FR4$_{D-VH}$-C$_{D-H}$ | VET224 | EVKLLESGGGLVQPGGSMRLSCAGSGFTFTDFYMNWIRQPAGKAPEWLGFIRDKAKGYTTEYNPSVKGRFTISRDNTQNMLYLQMNTLRAEDTATYYCAREGHTAAPFDYWGQGTLVTVSS |

| | | Sequence of mAb 231 |
|---|---|---|
| References | | |
| SEQ ID NO: 47 | | EVKLVESGGGLVQPGGSLKLSCATSGFTFSDYYMYWVRQTPEKRLEW VAYISNGGGSTYYPDTVKGRFTISRDNAKNTLYLQMSRLKSEDTAMY YCARHGGYYAMDYWGQGTSVTVSS |
| SEQ ID NO: 48 | | DIQMNQSPSSLSASLGDTITITCHASQNINVWLSWYQQKPGNIPKLLIY KASNLHTGVPSRFSGSGSGTGFTLTISSLQPEDIATYYCQQGQSYPLTFG GGTKLEIK |

| SEQ ID | Structure | Designation | Protein Sequence |
|---|---|---|---|
| | | Light Chain | |
| SEQ ID NO: 49 | FR1$_{M-VK}$-CDR1$_{M-VK}$-FR2$_{M-VK}$CDR2$_{M-VK}$-FR3$_{M-VK}$-CDR3$_{M-VK}$FR4$_{M-VK}$-C$_{D-L}$ | VET106 | DIQMNQSPSSLSASLGDTITITCHASQNI NVWLSWYQQKPGNIPKLLIYKASNLHT GVPSRFSGSGSGTGFTLTISSLQPEDIATY YCQQGQSYPLTFGGGTKLEIKGQPKASP SVTLFPPSSEELGANKATLVCLISDFYPS GVTVAWKADGSPITQGVETTKPSKQSN NKYAASSYLSLTPDKWKSHSSFSCLVTH EGSTVEKKVAPAECS |
| SEQ ID NO: 50 | FR1$_{M-VK}$-CDR1$_{M-VK}$-FR2$_{M-VK}$CDR2$_{M-VK}$-FR3$_{M-VK}$-CDR3$_{M-VK}$FR4$_{M-VK}$-C$_{D-K}$ | VET107 | DIQMNQSPSSLSASLGDTITITCHASQNI NVWLSWYQQKPGNIPKLLIYKASNLHT GVPSRFSGSGSGTGFTLTISSLQPEDIATY YCQQGQSYPLTFGGGTKLEIKNDAQPA VYLFQPSPDQLHTGSASVVCLLNSFYPK DINVKWKVDGVIQDTGIQESVTEQDKD STYSLSSTLTMSSTEYLSHELYSCEITHK SLPSTLIKSFQRSECQRVD |
| SEQ ID NO: 51 | FR1$_{M-VK}$-CDR1$_{M-VK}$-FR2$_{M-VK}$CDR2$_{M-VK}$-FR3$_{M-VK}$-CDR3$_{M-VK}$FR4$_{D-VL}$-C$_{D-L}$ | VET118 | DIQMNQSPSSLSASLGDTITITCHASQNI NVWLSWYQQKPGNIPKLLIYKASNLHT GVPSRFSGSGSGTGFTLTISSLQPEDIATY YCQQGQSYPLTFGGGTHLTVL |
| | | Heavy Chain | |
| SEQ ID NO: 52 | FR1$_{M-VH}$-CDR1$_{M-VH}$-FR2$_{M-VH}$CDR2$_{M-VH}$-FR3$_{M-VH}$-CDR3$_{M-VH}$FR4$_{M-VH}$-C$_{D-H}$ | VET217 | EVKLVESGGGLVQPGGSLKLSCATSGFT FSDYYMYWVRQTPEKRLEWVAYISNG GGSTYYPDTVKGRFTISRDNAKNTLYLQ MSRLKSEDTAMYYCARHGGYYAMDY WGQGTLVTVSS |
| SEQ ID NO: 53 | FR1$_{M-VH}$-CDR1$_{M-VH}$-FR2$_{M-VH}$CDR2$_{M-VH}$-FR3$_{M-VH}$-CDR3$_{M-VH}$FR4$_{D-VH}$-C$_{D-H}$ | VET218 | EVKLVESGGGLVQPGGSLKLSCATSGFT FSDYYMYWVRQTPEKRLEWVAYISNG GGSTYYPDTVKGRFTISRDNAKNTLYLQ MSRLKSEDTAMYYCARHGGYYAMDY WGQGTSVTVSS |

| | Constant Domain | Plasmid Designation | Sequence |
|---|---|---|---|
| SEQ ID NO: 54 | HC | VET214 | ASTTAPSVFPLAPSCGSTSGSTVALACLVSGYFPEP VTVSWNSGSLTSGVHTFPSVLQSSGLYSLSSMVT VPSSRWPSETFTCNVAHPASKTKVDKPVPKRENG RVPRPPDCPKCPAPEMLGGPSVFIFPPKPKDTLLIA RTPEVTCVVVDLDPEDPEVQISWFVDGKQMQTA KTQPREEQFNGTYRVVSVLPIGHQDWLKGKQFTC KVNNKALPSPIERTISKARGQAHQPSVYVLPPSRE ELSKNTVSLTCLIKDFFPPDIDVEWQSNGQQEPES KYRTTPPPQLDEDGSYFLYSKLSVDKSRWQRGDTF ICAVMHEALHNHYTQKSLSHSPGK |
| SEQ ID NO: 55 | Lambda LC | VET104 | GQPKASPSVTLFPPSSEELGANKATLVCLISDFYPS GVTVAWKADGSPITQGVETTKPSKQSNNKYAASS YLSLTPDKWKSHSSFSCLVTHEGSTVEKKVAPAE CS |

-continued

| | | | |
|---|---|---|---|
| SEQ ID NO: 56 | Kappa LC | VET105 | NDAQPAVYLFQPSPDQLHTGSASVVCLLNSFYPK DINVKWKVDGVIQDTGIQESVTEQDKDSTYSLSST LTMSSTEYLSHELYSCEITHKSLPSTLIKSFQRSEC QRVD |

| | | Constant Domain | Primer Designation | Primer Sequence |
|---|---|---|---|---|
| List of primers utilized for the antibody constant domain amplification from cDNA | | | | |
| SEQ ID NO: 57 | | HC | HC-F | GCCTCCACCACGGCCCC |
| SEQ ID NO: 58 | | | HC-R | TCATTTACCCGGAGAATGGG |
| SEQ ID NO: 59 | | Lambda LC | L-LC-F | GGTCAGCCCAAGGCCWMCC |
| SEQ ID NO: 60 | | | L-LC-R | CTAAGAGCACTCTGCRGGG |
| SEQ ID NO: 61 | | Kappa LC | K-LC-F | AATGATGCCCAGCCAGCCG |
| SEQ ID NO: 62 | | | K-LC-R | TTAGTCCACTCTCTGACACTC |

Canine CD20

| Region | SEQ ID | Primer Designation | Primer Sequence |
|---|---|---|---|
| CD20 | SEQ ID No: 63 | CD20 FL-F | 5'-TGAGATGACAACACCCAGAAA-3' |
| | SEQ ID No: 64 | CD20 FL-R | 5'-TTAAGGGATGCTGTCGTTTTC-3' |
| CD20 | SEQ ID No: 65 | CD20 Lp-F | 5'-AATATTACCATTTCCCATTTTTTTA-3' |
| Fragment | SEQ ID No: 66 | CD20 Lp-R | 5'-TATGCTGCCACAATATTGTATAG-3' |

Canine CD20

SEQ ID NO 67

MTTPRNSMSGTLPVDPMKSPTAMYPVQKIIPKRMPSVVGPTQNFFMRESKTLGAVQIMNGLF

HIALGSLLMIHTDVYAPICITMWYPLWGGIMFIISGSLLAAADKNPRKSLVKGKMIMNSLSLF

AAISGIIFLIMDIFNITISHFFKMENLNLIKAPMPYVDIHNCDPANPSEKNSLSIQYCGSIRSVFLG

VFAVMVIFTFFQKLVTAGIVENEWKKLCSKPKSDVVVLLAAEEKKEQPIETTEEMVELTEIAS

QPKKEEDIEIIPVQEEEEELEINFAEPPQEQESSPIENDSIP

```
        10         20         30         40         50         60
MTTPRNSMSG TLPVDPMKSP TAMYPVQKII PKRMPSVVGP TQNFFMRESK TLGAVQIMNG 70         80         90        100        110        120
LFHIALGSLL MIHTDVYAPI CITMWYPLWG GIMFIISGSL LAAADKNPRK SLVKGKMIMN 130        140        150        160        170        180
SLSLFAAISG IIFLIMDIFN ITISHFFKME NLNLIKAPMP YVDIHNCDPA NPSEKNSLSI 190        200        210        220        230        240
QYCGSIRSVF LGVFAVMVIF TFFQKLVTAG IVENEWKKLC SKPKSDVVVL LAAEEKKEQP 250        260        270        280        290
IETTEEMVEL TEIASQPKKE EDIEIIPVQE EEEELEINFA EPPQEQESSP IENDSIP
```

| SEQ ID NO | Amino Acid Sequence | Residue Positions in SEQ ID NO: 67 |
|---|---|---|
| Extracellular Domain | | |
| SEQ ID NO: 74 | TDVYAPIC | 74-81 |
| SEQ ID NO: 75 | NITISHFFKMENLNLIKAP MPYVDIHNCDPANPSEKN SLSIQYCGSIR | 140-187 |
| Epitope prediction using the Emboss Progam | | |
| SEQ ID NO: 76 | HTDVYAPICIT | 74-83 |
| SEQ ID NO: 77 | LSIQYCGSIRS | 178-211 |
| SEQ ID NO: 78 | LIKAPMPYVDIHNCDPA | 154-170 |
| SEQ ID NO: 79 | NITISHF | 140-146 |
| Epitope prediction using tools from Immuneepitope | | |
| SEQ ID NO: 80 | VDIHNCDPANPS | 162-173 |
| SEQ ID NO: 81 | KMENLNLIKAPM | 148-159 |
| SEQ ID NO: 82 | TISHFFKMENLN | 142-153 |
| SEQ ID NO: 83 | PMPYVDIHNCDP | 148-169 |
| SEQ ID NO: 84 | NCDPANPSEKNS | 166-177 |
| SEQ ID NO: 85 | YVDIHNCDPANPSEKN | 161-176 |

Feline CD20

SEQ ID NO: 63    CD20 FLF    TGAGATGACAACACCCAGAAA

SEQ ID NO: 68    FCD20R      GGATCCTTAAGGAATGCTATCGTTTT

The amino-acid sequence of the feline CD20 isolated from feline PBMC is as follows:

SEQ ID NO 69
MTTPRNSMSGTLPADAMKSPTAMNPVQKIIPKKMPSVVGPTQNFFMKESKPLGAVQIMNGL

FHMALGGLLMIHMEVYAPICMTVWYPLWGGIMYIISGSLLVAAEKNPRKSLVKGKMIMNSL

SLFAAISGMILLIMDIFNIAISHFFKMENLNLLKSPKPYIDIHTCQPESKPSEKNSLSIKY

CDSIRSVFLSIFAVMVVFTLFQKLVTAGIVENEWKKLCSKPKADVVVLLAAEEKKEQLVEI

TEEAVELTEVSSQPKNEEDIEIIPVQEEEEETEMNFPEPPQDQEPSLIENDSIP

Canine CD52:

| Primer Designation | Primer Sequence |
|---|---|
| CD52 F SEQ ID NO: 70 | CAACAAAGCTTGCCGCCACCATGAAGGGCTTCCTCTTCCT |
| CD52 R SEQ ID NO: 71 | CAACAGGATCCTCAGCTGAGGTAGAAGAGCT |

SEQ ID No 72
MKGFLFLLLTISLLVMIQIQTGVLGNSTTPRMTTKKVKSATPALSSLGGGSVLLFLANTLIQLF
YLS

```
         10         20         30         40         50         60
MKGFLFLLLT ISLLVMIQIQ TGVLGNSTTP RMTTKKVKSA TPALSSLGGG SVLLFLANTL

IQLFYLS
```

| SEQ ID | Sequence | Residue Position in SEQ ID NO 73 |
|---|---|---|
| SEQ ID NO: 86 | GGSVLLFLANTLIQLF | 49-64 |
| SEQ ID NO: 87 | FLFLLLTISLLVMIQ | 4-18 |
| SEQ ID NO: 88 | QTGVLGN | 20-26 |
| SEQ ID NO: 89 | KVKSATPALSSL | 36-47 |
| SEQ ID NO: 90 | PRMTTKKVKS | 30-39 | feline CD52 isolated from feline PBMC is as follows:
SEQ ID NO 73:

```
MKGFLFLLLTISLLVMIQIQTGVLGNTTTAATTTKKPKSATPPLSSLSSGSVLLFLANILVQLFY
LS 10          20          30          40          50          60
MKGFLFLLLT  ISLLVMIQIQ  TGVLGNTTTA  ATTTKKPKSA  TPPLSSLSSG  SVLLFLANIL

VQLFYLS
```

---

The invention claimed is:

1. A heterochimeric antibody, or fragment thereof, comprising, amino acid sequences of antibodies from a donor species of mammal and from a target species of mammal, wherein the donor species and the target species are different, comprising:
   a) a constant region sequence from a heavy chain and/or light chain identical to, or a conservative variant of, a sequence from the target species; and
   b) a variable domain sequence from a heavy chain and/or light chain, wherein said variable domain sequence comprises:
   i.) hypervariable region sequences comprising three complementarity determining regions (CDRs) as defined by Kabat, which are identical to, or a conservative variant of, CDRs from the donor species, and
   ii.) FR1, FR2, FR3, and FR4 framework sequences, wherein the FR1 and/or the FR4 sequence is identical to, or a conservative variant of, a FR1 and/or FR4 sequence from the target species, and the FR2 and FR3 sequences are identical to, or a conservative variant of, FR2 and FR3 sequences from the donor species;
wherein said variable domain sequence comprises at least three contiguous non-CDR residues corresponding to residues from the target species and at least three contiguous non-CDR residues corresponding to residues from the donor species,
   wherein the heterochimeric antibody or fragment thereof, comprises a heavy chain and a light chain, and the CDRs are from the same donor antibody.

2. The heterochimeric antibody of claim 1, wherein the donor is a mouse.

3. The heterochimeric antibody of claim 1, wherein the target is a companion animal.

4. The heterochimeric antibody of claim 3, wherein the companion animal is a dog, a cat or a horse.

5. The heterochimeric antibody of claim 3, wherein the heavy and/or light chain variable domain sequence comprises at least four contiguous non-CDR residues corresponding to residues found in antibodies from the target species.

6. The heterochimeric antibody of claim 3, wherein the heavy and/or light chain variable domain sequence comprises at least four contiguous non-CDR residues corresponding to residues found in antibodies from the donor species.

7. The heterochimeric antibody of claim 1, wherein the antibody binds to canine, feline or equine CD20.

8. The heterochimeric antibody of claim 7, wherein the antibody binds to an epitope on the extracellular loop of canine CD20.

9. The heterochimeric antibody of claim 1, wherein the antibody binds to canine, feline or equine CD52.

10. The heterochimeric antibody of claim 9, wherein the antibody binds to an epitope on the extracellular loop of canine CD52.

11. The heterochimeric antibody of claim 9, wherein said antibody binds to a canine CD52 antigen, wherein said canine CD52 antigen has an amino acid sequence according to SEQ ID NO: 72.

12. The heterochimeric antibody of claim 9, wherein said antibody binds to a feline CD52 antigen, wherein said feline CD52 antigen has an amino acid sequence according to SEQ ID NO: 73.

13. The heterochimeric antibody of claim 1, wherein the heterochimeric antibody comprises a light chain selected from the group consisting of:
   FR1-CDR1-FR2-CDR2-FR3-CDR3-FR4$_{T\text{-}Lambda}$-C$_{T\text{-}Lambda}$;
   FR1-CDR1-FR2-CDR2-FR3-CDR3-FR4$_{T\text{-}Kappa}$-C$_{T\text{-}Lambda}$;
   FR1-CDR1-FR2-CDR2-FR3-CDR3-FR4$_{T\text{-}Lambda}$-C$_{T\text{-}Kappa}$;
   FR1-CDR1-FR2-CDR2-FR3-CDR3-FR4$_{T\text{-}kappa}$-C$_{T\text{-}Kappa}$;
   FR1$_{T\text{-}Kappa}$-CDR1-FR2-CDR2-FR3-CDR3-FR4-C$_{T\text{-}Lambda}$;
   FR1$_{T\text{-}Lamba}$-CDR1-FR2-CDR2-FR3-CDR3-FR4-C$_{T\text{-}Lambda}$;
   FR1$_{T\text{-}Lambda\text{-}CD}$R1-FR2-CDR2-FR3-CDR3-FR4-C$_{T\text{-}Kappa}$;
   FR1$_{T\text{-}kappa\text{-}CDR}$1-FR2-CDR2-FR3-CDR3-FR4-C$_{T\text{-}Kappa}$;
   FR1$_{T\text{-}Lambda\text{-}CD}$-FR2-CDR2-FR3-CDR3-FR4$_{T\text{-}Lambda}$-C$_{T\text{-}Lambda}$; and
   FR1$_{T\text{-}kappa}$-CDR1-FR2-CDR2-FR3-CDR3-FR4$_{T\text{-}kappa}$-C$_{T\text{-}Kappa}$;
wherein T=Target species; Lambda=lambda light chain; Kappa=kappa light chain; C=Constant domain; FR=Framework region; CDR=Complementarity Determining Region; and wherein a FR is a donor species unless otherwise marked as a target species.

14. The heterochimeric antibody of claim 13, wherein said heterochimeric antibody is an anti-CD20 monoclonal antibody.

15. The heterochimeric antibody of claim 13, wherein said heterochimeric antibody is an anti-CD52 monoclonal antibody.

16. The heterochimeric antibody of claim 1, wherein the heterochimeric antibody comprises a heavy chain wherein said heavy chain is selected from the group consisting of:
   FR1-CDR1-FR2-CDR2-FR3-CDR3-FR4$_T$-C$_T$;
   FR1$_T$-CDR1-FR2-CDR2-FR3-CDR3-FR4-C$_T$; and
   FR1$_T$-CDR1-FR2-CDR2-FR3-CDR3-FR4$_T$-C$_T$;
   wherein T=Target species; Lambda=lambda light chain; Kappa=kappa light chain; C=Constant domain; FR=Framework region; CDR=Complementarity Determining Region; and wherein a FR is a donor species unless otherwise marked as a target species.

17. The heterochimeric antibody of claim 16, wherein said heterochimeric antibody is an anti-CD20 monoclonal antibody.

18. The heterochimeric antibody of claim 16, wherein said heterochimeric antibody is an anti-CD52 monoclonal antibody.

19. The heterochimeric antibody of claim 1, wherein the amino acid sequence of the FR4 light chain is selected from the group consisting of: SEQ ID NO: 1; SEQ ID NO: 2; SEQ ID NO: 3; SEQ ID NO: 4; SEQ ID NO: 5; SEQ ID NO: 6;

SEQ ID NO: 6; SEQ ID NO: 7; SEQ ID NO: 8; SEQ ID NO: 9; SEQ ID NO: 10; SEQ ID NO: 11; and SEQ ID NO: 12.

20. The heterochimeric antibody of claim 1, wherein the amino acid sequence of the FR4 heavy chain is selected from the group consisting of: SEQ ID NO: 13; SEQ ID NO: 14; SEQ ID NO: 15; SEQ ID NO: 16; SEQ ID NO: 17; SEQ ID NO: 18; and SEQ ID NO:19.

21. The heterochimeric antibody of claim 1, wherein the amino acid sequence of the FR1 light chain is selected from the group consisting of: SEQ ID NO: 20; SEQ ID NO: 21; SEQ ID NO: 22; SEQ ID NO: 23; SEQ ID NO: 24; and SEQ ID NO: 25.

22. The heterochimeric antibody of claim 1, wherein the amino acid sequence of the FR1 heavy chain is selected from the group consisting of: SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; and SEQ ID NO: 40.

23. The heterochimeric antibody of claim 1, wherein said antibody comprises a light chain with an amino acid sequence selected from the group consisting of: SEQ ID NO: 41; SEQ ID NO: 42; SEQ ID NO: 43; SEQ ID NO: 44; SEQ ID NO: 45; and SEQ ID NO: 46.

24. The heterochimeric antibody of claim 1, wherein the heterochimeric antibody is derived from a rat anti-human CD52 antibody and wherein the heterochimeric antibody comprises a sequence selected from the group consisting of:

$FR1_{R-VK}$-$CDR1_{R-VK}$-$FR2_{R-VK}$-$CDR2_{R-VK}$-$FR3_{R-VK}$-$CDR3_{R-VK}$-$FR4_{R-VK}$-$C_{D-L}$;

$FR1_{D-VL}$-$CDR1_{R-VK}$-$FR2_{R-VK}$-$CDR2_{R-VK}$-$FR3_{R-VK}$-$CDR3_{R-VK}$-$FR4_{D-VL}$-$C_{D-L}$;

$FR1_{R-VL}$-$CDR1_{R-VK}$-$FR2_{R-VK}$-$CDR2_{R-VK}$-$FR3_{R-VK}$-$CDR3_{R-VK}$-$FR4_{D-VL}$-$C_{D-L}$;

$FR1_{R-VH}$-$CDR1_{R-VH}$-$FR2_{R-VH}$-$CDR2_{R-VH}$-$FR3_{R-VH}$-$CDR3_{R-VH}$-$FR4_{R-VH}$-$C_{D-H}$;

$FR1_{D-VH}$-$CDR1_{R-VH}$-$FR2_{R-VH}$-$CDR2_{R-VH}$-$FR3_{R-VH}$-$CDR3_{R-VH}$-$FR4_{D-VH}$-$C_{D-H}$; and $FR1_{R-VH}$-$CDR1_{R-VH}$-$FR2_{R-VH}$-$CDR2_{R-VH}$-$FR3_{R-VH}$-$CDR3_{R-VH}$-$FR4_{D-VH}$-$C_{D-H}$;

wherein R: Rat; D: Dog; $FR_{R-VK}$=Rat kappa light chain (LC) FR; $FR_{D-VL}$=Canine lambda LC FR; $CDR_{R-VK}$=Rat kappa LC CDR; $CDR_{R-VH}$=CDR from a rat heavy chain (HC); $CD_{D-L}$ or $CD_{D-K}$=Constant domain from a canine lambda or canine kappa LC; $CD_{D-H}$=Constant domain from canine HC.

25. The heterochimeric antibody of claim 1, wherein the heterochimeric antibody is derived from mouse anti-canine lymphoma mab 231 antibody and wherein the heterochimeric antibody comprises a sequence selected from the group consisting of:

$FR1_{M-VK}$-$CDR1_{M-VK}$-$FR2_{M-VK}$-$CDR2_{M-VK}$-$FR3_{M-VK}$-$CDR3_{M-VK}$-$FR4_{M-VK}$-$C_{D-L}$;

$FR1_{M-VK}$-$CDR1_{M-VK}$-$FR2_{M-VK}$-$CDR2_{M-VK}$-$FR3_{M-VK}$-$CDR3_{M-VK}$-$FR4_{M-VK}$-$C_{D-K}$;

$FR1_{M-VK}$-$CDR1_{M-VK}$-$FR2_{M-VK}$-$CDR2_{M-VK}$-$FR3_{M-VK}$-$CDR3_{M-VK}$-$FR4_{D-VL}$-$C_{D-L}$;

$FR1_{M-VH}$-$CDR1_{M-VH}$-$FR2_{M-VH}$-$CDR2_{M-VH}$-$FR3_{M-VH}$-$CDR3_{M-VH}$-$FR4_{M-VH}$-$C_{D-H}$; and $FR1_{M-VH}$-$CDR1_{M-VH}$-$FR2_{M-VH}$-$CDR2_{M-VH}$-$FR3_{M-VH}$-$CDR3_{M-VH}$-$FR4_{D-VH}$-$C_{D-H}$;

wherein M: Mouse; D: Dog; $FR_{M-VK}$=Murine kappa LC FR; $FR_{D-VL}$=FR Canine lambda LC FR; $CDR_{M-VK}$=Murine kappa LC CDR; $CDR_{M-VH}$=Murine HC CDR; $CD_{D-L}$ or $CD_{D-K}$=Constant domain from a canine lambda or canine kappa LC; $CD_{D-H}$=Constant domain from a canine HC.

26. The heterochimeric antibody of claim 25, comprising one or more amino acid sequences selected from the group consisting of: SEQ ID NO: 47, SEQ ID NO: 48; SEQ ID NO: 49; SEQ ID NO: 50; SEQ ID NO: 51; SEQ ID NO: 52; and SEQ ID NO: 53.

27. The heterochimeric antibody of claim 1, wherein the donor species antibody is a murine anti-canine CD20 antibody.

28. The heterochimeric antibody of claim 27, wherein said antibody binds to a canine CD20 antigen, wherein said canine CD20 antigen has an amino acid sequence according to SEQ ID NO: 67.

29. The heterochimeric antibody of claim 28, wherein said antibody binds to an epitope region on a canine CD20 selected from the group consisting of SEQ ID NOS 76-85.

30. The heterochimeric antibody of claim 27, wherein said antibody binds to a feline CD20 antigen, wherein said feline CD20 antigen has an amino acid sequence according to SEQ ID NO: 69.

31. A pharmaceutical composition comprising an antibody according to claim 1.

* * * * *